US00RE50908E

(19) United States
(12) Reissued Patent
Dranoff et al.

(10) Patent Number: US RE50,908 E
(45) Date of Reissued Patent: Jun. 9, 2026

(54) VACCINE COMPOSITIONS AND METHODS FOR RESTORING NKG2D PATHWAY FUNCTION AGAINST CANCERS

(71) Applicant: Dana-Farber Cancer Institute, Inc., Boston, MA (US)

(72) Inventors: Glenn Dranoff, Sudbury, MA (US); Kai W. Wucherpfennig, Brookline, MA (US); Christopher Harvey, Boston, MA (US); F. Stephen Hodi, Framingham, MA (US)

(73) Assignee: Dana-Farber Cancer Institute, Inc., Boston, MA (US)

(21) Appl. No.: 17/314,828

(22) Filed: May 7, 2021

Related U.S. Patent Documents

Reissue of:
(64) Patent No.: 10,279,021
Issued: May 7, 2019
Appl. No.: 15/125,882
PCT Filed: Mar. 16, 2015
PCT No.: PCT/US2015/020694
§ 371 (c)(1),
(2) Date: Sep. 13, 2016
PCT Pub. No.: WO2015/139020
PCT Pub. Date: Sep. 17, 2015

U.S. Applications:
(60) Provisional application No. 61/953,064, filed on Mar. 14, 2014.

(51) Int. Cl.
*A61K 39/00* (2006.01)
*A61K 45/06* (2006.01)
*C07K 14/705* (2006.01)
*C07K 14/74* (2006.01)

(52) U.S. Cl.
CPC ..... *A61K 39/0011* (2013.01); *A61K 45/06* (2013.01); *C07K 14/70539* (2013.01); *A61K 2039/5152* (2013.01); *A61K 2039/6037* (2013.01)

(58) Field of Classification Search
CPC ..... A61K 45/06; A61K 39/0011; C07K 14/70539
See application file for complete search history.

(56) References Cited

U.S. PATENT DOCUMENTS 4,816,567 A 3/1989 Cabilly et al.
5,122,464 A 6/1992 Wilson et al.
5,225,539 A 7/1993 Winter
5,530,101 A 6/1996 Queen et al.
5,545,403 A 8/1996 Page
5,545,405 A 8/1996 Page
5,545,806 A 8/1996 Lonberg et al.
5,545,807 A 8/1996 Surani et al.
5,569,825 A 10/1996 Lonberg et al.
5,585,089 A 12/1996 Queen et al.
5,591,639 A 1/1997 Bebbington
5,624,821 A 4/1997 Winter et al.
5,625,126 A 4/1997 Lonberg et al.
5,633,425 A 5/1997 Lonberg et al.
5,648,260 A 7/1997 Winter et al.
5,658,759 A 8/1997 Bebbington
5,661,016 A 8/1997 Lonberg et al.
5,677,425 A 10/1997 Bodmer et al.
5,693,762 A 12/1997 Queen et al.
5,714,350 A 2/1998 Co et al.
5,766,886 A 6/1998 Studnicka et al.
5,869,046 A 2/1999 Presta et al.
5,939,598 A 8/1999 Kucherlapati et al.
5,981,216 A 11/1999 Kenten et al.
5,998,144 A 12/1999 Reff et al.
6,075,181 A 6/2000 Kucherlapati et al.
6,091,001 A 6/2000 Jakobovits et al.
6,114,598 A 9/2000 Kucherlapati et al.
6,121,022 A 9/2000 Presta et al.
6,165,745 A 12/2000 Ward et al.
6,180,370 B1 1/2001 Queen et al.
6,194,551 B1 2/2001 Idusogie et al.
6,277,375 B1 8/2001 Ward
6,344,203 B1 * 2/2002 Sandrin ..... C07K 7/06 424/184.1
6,350,861 B1 2/2002 Co et al.
6,737,056 B1 5/2004 Presta
7,317,091 B2 1/2008 Lazar et al.
7,771,718 B2 8/2010 Spies et al.
7,959,916 B2 6/2011 Spies et al.
8,101,720 B2 1/2012 Lazar et al.
8,182,809 B1 5/2012 Wu
9,402,905 B2 8/2016 Wucherpfennig et al. ..... A61P 35/00
10,106,611 B2 10/2018 Wucherpfennig et al. ..... A61P 35/00

(Continued)

FOREIGN PATENT DOCUMENTS

CN 102911270 2/2013
CN 102911270 A 2/2013

(Continued)

OTHER PUBLICATIONS

Qi et al., Scandinavian J. of Immunol., 58:211-220, 2003.*
Nassal et al. Int. J. of Med. Microbiol., 298:135-42, 2008.*
Ali et al., Nature Materials 8:151-158, 2009.*
Groh, V. et al., Efficient cross-priming of tumor anigen-specific T cells by dendritic cells sensistized with diverse anti-MICA opsonized tumor cells. Proc. Nat'l Acad. Sci., 102(18):6461-6466 (2005).

(Continued)

*Primary Examiner* — Padmashri Ponnaluri
(74) *Attorney, Agent, or Firm* — Baker Donelson

(57) ABSTRACT

The present invention provides compositions and methods for treating cancer in a subject by eliciting an immune response against a MIC polypeptide.

27 Claims, 7 Drawing Sheets

Specification includes a Sequence Listing.

(56) References Cited

U.S. PATENT DOCUMENTS

| | | | | |
|---|---|---|---|---|
| 10,745,483 | B2 * | 8/2020 | Wucherpfennig | C07K 16/3069 |
| 10,851,148 | B2 * | 12/2020 | Cheney | C07K 14/705 |
| 2003/0022450 | A1 | 1/2003 | Pan et al. | |
| 2003/0099647 | A1 | 5/2003 | Deshpande et al. | |
| 2003/0118592 | A1 | 6/2003 | Ledbetter et al. | |
| 2003/0133939 | A1 | 6/2003 | Ledbetter et al. | |
| 2003/0153043 | A1 | 8/2003 | Carr et al. | |
| 2003/0165835 | A1 | 9/2003 | Spies et al. | |
| 2004/0067503 | A1 | 4/2004 | Tan et al. | |
| 2004/0115198 | A1 | 6/2004 | Spies et al. | |
| 2005/0053608 | A1 | 3/2005 | Weber et al. | |
| 2005/0059087 | A1 | 3/2005 | Weber et al. | |
| 2005/0158307 | A1 | 7/2005 | Spies et al. | |
| 2005/0233391 | A1 | 10/2005 | Spies et al. | |
| 2006/0024297 | A1 | 2/2006 | Wood et al. | |
| 2006/0228349 | A1 | 10/2006 | Acton et al. | |
| 2006/0246071 | A1 | 11/2006 | Green et al. | |
| 2007/0248607 | A1 | 10/2007 | Spies et al. | |
| 2008/0148432 | A1 | 6/2008 | Abad | |
| 2009/0022644 | A1 | 1/2009 | Sweredjuk | |
| 2009/0175821 | A1 | 7/2009 | Bridon et al. | |
| 2009/0226447 | A1 | 9/2009 | Boone et al. | |
| 2009/0252729 | A1 | 10/2009 | Farrington et al. | |
| 2010/0111973 | A1 | 5/2010 | Dranoff et al. | |
| 2010/0189711 | A1 | 7/2010 | Dranoff et al. | |
| 2010/0261269 | A1 | 10/2010 | June et al. | |
| 2011/0311561 | A1 | 12/2011 | Martin, Jr. et al. | |
| 2012/0100182 | A1 | 4/2012 | Mooney | |
| 2012/0315287 | A1 | 12/2012 | Wu | |
| 2013/0202707 | A1 | 8/2013 | Ali et al. | |
| 2014/0004112 | A1 | 1/2014 | Wucherpfennig et al. | |
| 2014/0027630 | A1 | 1/2014 | Musselman | |
| 2014/0037630 | A1 | 2/2014 | Dranoff et al. | |
| 2016/0046716 | A1 | 2/2016 | Wucherpfennig et al. | |
| 2017/0008962 | A1 | 1/2017 | Wucherpfennig et al. | |
| 2017/0022275 | A1 | 1/2017 | Wucherpfennig et al. | |
| 2017/0198054 | A1 | 7/2017 | Harvey et al. | |

FOREIGN PATENT DOCUMENTS

| | | | | |
|---|---|---|---|---|
| EP | 0 154 316 | | 9/1985 | |
| EP | 0 401 384 | | 12/1990 | |
| EP | 1 176 195 | | 1/2002 | |
| EP | 2 336 180 | | 6/2011 | |
| JP | 2008-543774 | | 12/2008 | |
| JP | 2008-543774 | A | 12/2008 | |
| WO | WO 88/07054 | | 3/1988 | |
| WO | WO 88/08089 | | 10/1988 | |
| WO | WO 91/10741 | | 7/1991 | |
| WO | WO 94/02602 | | 2/1994 | |
| WO | WO 94/29351 | | 12/1994 | |
| WO | WO 96/32478 | | 10/1996 | |
| WO | WO 96/33735 | | 10/1996 | |
| WO | WO 97/34631 | | 9/1997 | |
| WO | WO98/19167 | | 5/1998 | |
| WO | WO 98/19167 | A2 | 5/1998 | |
| WO | WO 98/24893 | | 6/1998 | |
| WO | WO99/051642 | | 10/1999 | |
| WO | WO 99/051642 | A1 | 10/1999 | |
| WO | WO99/54342 | | 10/1999 | |
| WO | WO 99/54342 | A1 | 10/1999 | |
| WO | WO00/42072 | | 7/2000 | |
| WO | WO 00/42072 | A2 | 7/2000 | |
| WO | WO01/58957 | | 8/2001 | |
| WO | WO 01/58957 | A2 | 8/2001 | |
| WO | WO02/06919 | | 1/2002 | |
| WO | WO 02/06919 | A2 | 1/2002 | |
| WO | WO02/068615 | | 9/2002 | |
| WO | WO 02/068615 | A2 | 9/2002 | |
| WO | WO 03/035835 | | 5/2003 | |
| WO | WO 03/041600 | | 5/2003 | |
| WO | WO 2003/074679 | | 9/2003 | |
| WO | WO 03/089616 | | 10/2003 | |
| WO | WO 04/016750 | | 2/2004 | |
| WO | WO 04/035752 | | 4/2004 | |
| WO | WO 2004/029207 | | 4/2004 | |
| WO | WO2004/035752 | | 4/2004 | |
| WO | WO 2004/035752 | A2 | 4/2004 | |
| WO | WO 04/063351 | | 7/2004 | |
| WO | WO 04/074455 | | 9/2004 | |
| WO | WO 2004/099249 | | 11/2004 | |
| WO | WO 05/040217 | | 5/2005 | |
| WO | WO 05/070963 | | 8/2005 | |
| WO | WO 05/092925 | | 10/2005 | |
| WO | WO 06/020114 | | 2/2006 | |
| WO | WO2006/068953 | | 6/2006 | |
| WO | WO 2006/068953 | A2 | 6/2006 | |
| WO | WO2006/133396 | | 12/2006 | |
| WO | WO 2006/133396 | A2 | 12/2006 | |
| WO | WO 2007/055926 | | 5/2007 | |
| WO | WO 2008/036981 | | 3/2008 | |
| WO | WO2010/069532 | | 6/2010 | |
| WO | WO 2010/069532 | A1 | 6/2010 | |
| WO | WO2011/014469 | | 2/2011 | |
| WO | WO 2011/014469 | A1 | 2/2011 | |
| WO | WO 2011/063336 | | 5/2011 | |
| WO | WO 2013/049517 | | 4/2013 | |
| WO | WO 2013/117647 | | 8/2013 | |
| WO | WO2014/144791 | | 9/2014 | |
| WO | WO 2014/144791 | A2 | 9/2014 | |
| WO | WO-2014140904 | A2 * | 9/2014 | A61P 31/12 |

OTHER PUBLICATIONS

Jinushi, M. et al., "Impairment of natural killer cell and dendritic cell functions by the soluble form of MHC class lelated chain A in advanced human hepatocellular carcinomas", J of Hepatology, 43:1013-1020 (2005).

Jinushi, M. et al., "Therapy-induced antibodies to MHC class I chain-related protein A antagonize immune suppression and stimulate antitumor cytotoxicity" Proc. Nat'l Acad. Sci., 103(24):9190-9195 (2006).

Balmana et al. "BRCA in breast cancer: ESMO Clinical Recommendations", Annals of Oncology 20(supplement 4):v19-20 (2009).

Bednsten et al. "Improved Prediction of Signal Peptides: SignalP 3.0", J Mol Biol 340(4) 783-95 (2004).

Dall'Acqua et et al., "Properties of Human IgG1s Engineered for Enhanced Binding to the Neonatal Fc Receptor (FcRn)", Journal of Biological Chemistry 281:23514-23524 (2006).

Wang, X. et al., "An six-amino acid motif in the .alpha.3 domain of MICA is the cancer therapeutic target to inhibit shedding," Biochemical and Biophysical Research Communications, 387:476-481 (2009).

Pantazes, R.J. et al., "OptCDR: a general computational method for the design of antibody complementarity determining regions for targeting epitope binding," Protein Engineering, Design & Selection, 23(11):849-353 (2010).

Sarmay et al. "Mapping and Comparison of the Interaction Sites on the Fc Region of IgG Responsible for Triggering Antibody Dependent Cellular Cytotoxicity (ADCC) through Different Types of Human Fc.gamma. Receptor", Molec. Immunol. 29 (5): 633-9 (1992).

Shields, R.L. et al. "Lack of Fucose on Human IgG1 N-Linked Oligosaccharide Improves Binding to Human Fc.gamma. RIII and Antibody-dependent Cellular Toxicity", J Biol. Chem. 277:26733-26740 (2002).

Tao et al., "Structural Features of Human Immunoglobulin G that Determine Isotype-specific Differences in Complement Activation", J. Exp. Med. 178:661 (1993).

Leblond et al.,"The amphipathic alpha-helical repeats of apolipoprotein A-I are responsible for binding of high density ipoproteins to HepG2 cells," J. Biol. Chem., 266 (10): 6058-6067 (1991).

Qi et al (Scandinavian Journal of Immunology, 2003, vol. 58, pp. 211-220) (Year: 2003).*

Ali et al (Nature Materials, 2009, vol. 8, pp. 151-158) (Year: 2009).*

Vetter et al (Journal of Investigative Dermatology, 2002, vol. 118, pp. 600-605) (Year: 2002).*

(56) References Cited

OTHER PUBLICATIONS

Gonzalez et al (Annals of Oncology, 1998, vol. 9, pp. 431-435) (Year: 1998).*
Nassal et al (International Journal of Medical Microbiology, 2008, vol. 298, pp. 135-142) (Year: 2008).*
May et al., "Isolation of human anti-MICA antibody from cancer patients responding to immunotherapies," Journal of Clinical Oncology, 30(15) Suppl., Abstract No. 2502 (2012).
Liu, G. et al., "Cutting Edge: The Membrane type Matrix Metalloproteinase MMP14 Mediates Constitutive Shedding of MHC Class I Chain-Related Molecule A Independent of a Disintegrin and Metalloproteinases," J. Immunol., 184:3346-3350 (2010).
U.S. Appl. No. 61/792,034, filed Mar. 15, 2013, Wucherpfennig et al.
U.S. Appl. No. 61/913,198, filed Dec. 6, 2013, Wucherpfennig et al.
Ali et al. "In Situ Regulation of DC Subsets and T Cells Mediates Tumor Regression in Mice", Science Translation Medicine, 1, 8ra19, 12 pages (2009).
Altschul et al. "Basic Local Alignment Search Tool", J. Mol. Biol., 215:403-10 (1990).
Almagro et al., "Humanization of antibodies", Frontiers in Bioscience, 13:1619-33 (2008).
Altschul et al., "Gapped BLAST and PSI-BLAST: a new generation of protein database search programs", Nucleic Acids Res. 25(17):3389-3402 (1997).
Amanna et al., "Duration of Humoral Immunity to Common Viral and Vaccine Antigens", N. Engl. J. Med., 357:1903-1915, (2007).
Andrade et al., "Adsorption of complex proteins at interfaces", Pure and Appl. Chem., 64(11):1777-1781 (1992).
Araya, C. L. et al., "Deep mutational scanning: assessing protein function on a massive scale," Trends Biotechnol., 29(9), pp. 435-442 (2011).
Balazs et al., "Antibody-based protection against HIV infection by vectored immunoprophylaxis", Nature, 481(7379):81-4 (2011).
Banchereau et al. "Long-Term Human B Cell Lines Dependent on Interleukin-4 and Antibody to CD40", Science 251 70 (1991).
Barbas, S. et al., "Recognition of DNA by Synthetic Antibodies," J. Am. Chem. Soc., vol. 116(5), pp. 2161-2162 (1994).
Beiboer, S. et al., "Guided Selection of a Pan Carcinoma Specific Antibody Reveals Similar Binding Characteristics yet Structural Divergence Between the Original Murine Antibody and its Human Equivalent," JMB, 296: 833-849 (2000).
Benjamin et al. "The Antigenic Structure of Proteins: A Reappraisal", Ann Rev Immunol 2 67-101, (1984).
Bergers et al., "Extrinsic regulators of epithelial tumor progression: metalloproteinases," Curro Opinions in Genetics and Development, 10: 120-127 (2000).
Bird et al. "Single-Chain Antigen-Binding Proteins", Science 242:423-426 (1988).
Bisman et al., "Long-term presence of memory B-cells specific for different vaccine components", Vaccine, 28:179-186 (2009).
Bodey, B. et al., "Failure of Cancer Vaccines: The Significant Limitations of this Approach to Immunotherapy," Anticancer Research, 20: 2665-2676 (2000).
Boemer et al, "Production of antigen-specific human monoclonal antibodies from in vitro-primed human splenocytes", J Immunol, 147(1) 86 95 (1991).
Bordo et al. "Suggestions for "Safe" Residue Substitutions in Site-Directed Mutagenesis", J. Mol. Biol. 217:721-729 (1991).
Brown, M. et al., "Tolerance to single, but not multiple, amino acid replacements in antibody VH CDR 2 a means of minimizing B cell wastage from somatic hypermutation?," J Immunol., vol. 156(9), pp. 3285-3291 (1996).
Caine et al., "Recombinant Human Phenylethanolamine N-Methyltransferase: Overproduction in *Escherichia coli*, Purification, and Characterization", Protein Expression and Purification 8(2) 159 166 (1996).
Canfield "The Binding Affinity of Human IgG for its High Affinity Fc Receptor Is Determined by Multiple Amino Acids in the CH2 Domain and Is Modulated by the Hinge Region", J. Exp. Med. 173:1483 (1991).
Cao et al., "An optimized assay for the enumeration of antigen-specific memory B cells in different compartments of the human body", Journal of Immunological Methods, 358:56-65 (2010).
Casset, F. et al., "A peptide mimetic of an anti-CD4 monoclonal antibody by rational design," BBRC, vol. 307, pp. 198-205(2003).
Champe et al. "Monoclonal Antibodies That Block the Activity of Leukocyte Function-associated Antigen 1 Recognize Three Discrete Epitopes in the Inserted Domain of CD11a", The Journal of Biological Chemistry, 270:1388-1394 (1995).
Chen, C. et al., "Generation and Analysis of Random Point Mutations in an Antibody CDR2 Sequence: Many Mutated Antibodies Lose Their Ability to Bind Antigen," J Exp. Med., vol. 176, pp. 855-866 (1992).
Chen, Y. et al, "Selection and analysis of an optimized anti-VEGF antibody: crystal structure of an affinity-matured Fabin complex with antigen," J Mol. Biol., vol. 293, pp. 865-881 (1999).
Cheung et al., "Epitope-Specific Antibody Response to the Surface Antigen of Duck Hepatitis B Virus in Infected Ducks", Virology 176:546 (1990).
Chin et al., "Immune intervention with monoclonal antibodies targeting CD152 {CTLA-4) for autoimmune and malignant diseases," Chang Gung Med J., 31 (1): 1-15 (2008).
Choi et al., "Evolutionary conservation in multiple faces of protein interaction", Proteins: Structure, Function, and Bioinformatics, 77(1):14-25 (2009).
Chothia et al., "Conformations of immunoglobin hypervariable regions", Nature, 342:877-883 (1989).
Chothia, C. et al., "Structural Repertoire of the Human VH Segments," J Mol. Biol., vol. 227, pp. 799-817 (1992).
Chothia et al. "Canonical Structures for the Hypervariable Regions", J Mol Biol 196 901-917 (1987).
Clackson et al, "Making antibody fragments using phage display libraries", Nature, 352 624-628 (1991).
Cole et al, "The EBV-Hybridoma Technique and its Application to Human Lung Cancer", Monoclonal Antibodies and Cancer Therapy, p. 77-96 (1985).
Corada et al., "Monoclonal antibodies directed to different regions of vascular endothelial cadherin extracellular domain affect adhesion and clustering of the protein and modulate endothelial permeability", Blood; 97:1679-84 (2001).
Corti et al., "Analysis of Memory B Cell Responses and Isolation of Novel Monoclonal Antibodies with Neutralizing Breadth from HIV-1-Infected Individuals", PLoS One, 5:e8805 (2010).
Cox et al., "Glycan optimization of a human monoclonal antibody in the aquatic plant Lemna minor", Nat. Biotechnol 24(12): 1591-7 (2006).
Cox, J. P. L. et al. "A Directory of Human Germ-line VH Segments Reveals a Strong Bias in their Usage" Eur. J Immunol. 24:827-836 (1994).
Crotty et al., "Cutting Edge: Long-Term B Cell Memory in Humans after Smallpox Vaccination" J. Immunol., 171:4969-4973 (2003).
Cunningham et al. "High-Resolution Epitope Mapping of hGH-Receptor Interactions by Alanine-Scanning Mutagenesis", Science 244: 1081-1085 (1989).
Dall'Acqua et al. "Increasing the Affinity of a Human IgG1 for the Neonatal Fc Receptor: Biological Consequences", Journal of Immunology, 169:5171-5180 (2002).
De Genst et al., "Antibody repertoire development in camelids", Dev Comp Immunol; 30:187-98 (2006).
De Pascalis, R. et al, "Grafting of "abbreviated" complementarity-determining regions containing specificity-determining residues essential for ligand contact to engineer a less immunogenic humanized monoclonal antibody," The Journal of Immunology, 169: 3076-3084 (2002).
De Ridder G. et al. "Cell-Surface GRP78 and its Antibodies: Pathologic and Therapeutic Roles in Cancer", 2010. Retrieved from the Internet: URL:http://dukespace.lib.duke.edu/dspace/bitstream/handle/10161 /3805/deRidder_duke_0066D_10579.pdf?sequence=1.

(56) References Cited

OTHER PUBLICATIONS

Dennis, C. "Off by a whisker", Nature, vol. 442, pp. 739-741 (2006).
Ditzel, H. et al., "Determinants of Polyreactivity in a Large Panel of Recombinant Human Antibodies from HIV-Infection," The Journal of Immunology, vol. 157, pp. 739-749, (1996).
Doubrovina et al., "Evasion from NK Cell Immunity by MHC Class I Chainrelated Molecules Expressing Colon Adenocarcinoma," J Immunol, 171:6891-9 (2003).
Duncan et al., "Localization of the binding site for the human high-affinity Fe receptor on IgG", Nature 332:563 (1988).
Duquesnoy, R. et al., "Structurally based epitope analysis of major histocompatibility complex class I-related chain A (MICA) antibody specificity patterns," Human Immunology, vol. 69:826-832 (2008).
Emim et al. "Antigenic Conservation and Divergence between the Viral-Specific Proteins of Poliovirus Type 1 and Various Picornaviruses", Virology 140 13-20 (1985).
Fang et al. "Stable antibody expression at therapeutic levels using the 2A peptide", Nature Biotechnology 23, 584-590 ((2005).
Fecteau et al., "Peripheral blood CD27+ IgG+ B cells rapidly proliferate and differentiate into immunoglobulin-secreting cells after exposure to low CD154 interaction", Immunology, 128:e353-e365 30 (2009).
Fields et al., Chapter 3 "Synthetic Peptides: A User's Guide", p. 77 (1992).
Fishwild et al, "High-avidity human IgGk monoclonal antibodies from a novel strain of minilocus transgenic mice", Nature Biotechnology 14, 845-51 (1996).
Fonseca, C. et al., "Protein disulfide isomerases are antibody targets during immune-mediated tumor destruction", Blood, vol. 113, pp. 1681-1688 (2009).
Franz et al. "Ex vivo characterization and isolation of rare memory B cells with antigen tetramers", Blood, 118(2):348-357 (2011).
Germain, C. et al., "MHC Class I-Related Chain a Conjugated to Antitumor Antibodies Can Sensitize Tumor Cells to Specific Lysis by Natural Killer Cells," Clinical Cancer Research, The American Association for Cancer Research, US, vol. 11 (20), pp. 7516-7522, Oct. 15, 2005.
Getzoff et al. "The Chemistry and Mechanism of Antibody Binding to Protein Antigens", Advances in Immunology 43:1-98, (1988).
Gillies S.D. et al., "Improving the Efficacy of Antibody-Interleukin 2 Fusion Proteins by Reducing Their Interaction with Fc Receptors", Cancer Res. 59:2159-66 (1999).
Girlanda, S. et al., "MICA Expressed by Multiple Myeloma and Monoclonal Gammopathy of Undetermined Significance Plasma Cells Costimulates Pamidronate-activated Gammadelta Lymphocytes," Cancer Research, vol. 65 (16), pp. 7502-7508 (2005).
Gong et al., "A protein domain interaction interface database: InterPare", BMC: Bioinformatics, 6:1471-2105 (2007).
Groh et al., "Tumour-derived Soluble MIC Ligands Impair Expression of NKG2D and T-cell Activation," Nature 419: 734-8 (2002).
Groh, V. et al., "Broad tumor-associated expression and recognition by tumor-derived gammadelta T cells of MICA and MICB," Proc. Natl. Acad. Sci. USA, vol. 96:6879-6884 (1999).
Groh, V. et al., "Cell stress-regulated human major histocompatibility complex class I gene expressed in Jastrointestinal epithelium," Proc. Natl. Acad. Sci. USA, 93:12445-12450 (1996).
Groh, V. et al., "Recognition of Stress-Induced MHC Molecules by Intestinal Epithelial gammadelta T Cells," Science, 279:1737-1740 (1998).
Guo et al., "Protein tolerance to random amino acid change", Proc. Natl. Acad. Sci., USA, 101(25):9205-9210 (2004).
Gura, T. "Systems for Identifying New Drugs are Often Faulty", Science, 278: 1041-1042 (1997).
Hara et al., "Interleukin-2 potentiation of cetuximab antitumor activity for epidermal growth factor receptor-overexpressing gastric cancer xenografts through antibody-dependent cellular cytotoxicity," Cancer Sci., 99 (7):171-478 (2008).
Henn et al., "Modulation of Single-Cell IgG Secretion Frequency and Rates in Human Memory B Cells by CpG DNA, CD40L, IL-21, and Cell Division", J. Immunol., 183:31777-3187 (2009).
Hinton et al. "An Engineered Human IgG1 Antibody with Longer Serum Half-Life", Journal of Immunology 176:346-356 (2006).
Hinton et al., "Engineered Human IgG Antibodies with Longer Serum Half-lives in Primates", J. Biol. Chem. 279(8): 6213-6216 (2004).
Hofer et al., Adaptation of humoral memory, Immunological Reviews, 211:295-302 (2006).
Hofmann et al. "A database of membrane spanning proteins segments", Biol Chem Hoppe-Seyler 374,166 (1993).
Holm, P. et al. "Functional mapping and single chain construction of the anti-cytokeratin 8 monoclonal antibody TS1" Mol. Immunol., 44:1075-1084 (2007).
Hoogenboom et al. "Human Antibodies from Synthetic Repertoires of Germline VH Gene Segments Rearranged in Vitro", J Mol Biol, 227 381 (1991).
Hopp et al. "A computer program for predicting protein antigenic determinants", Molecular Immunology 20 483-489 (1983).
Hopp et al. "Prediction of protein antigenic determinants from amino acid sequences", Proc Natl Acad Sci USA 78 3824-3828 (1981).
Hopp, Methods for identifying antigenic determinants and other interaction sites, Immunol Methods 88 1-18 (1986).
Hue, S. et al., "Potential Role of NKG2D/MHC Class I-Related Chain A Interaction in Intrathymic Maturation of Single-Positive COB T Cells," The Journal of Immunology, 171:1909-1917 (2003).
Huergo-Zapico L. et al. "Expression of ERp5 and GRP78 on the membrane of chronic lymphocytic leukemia cells: association with soluble MICA shedding", Cancer Immunology, Immunotherapy, 61(8):1201-1210 (2012).
Huggins et al., "CpG DNAactivation and plasma-cell differentiation of CD27_naïve human B cells", Blood, 109:1611-1619 (2007).
Huston et al. "Protein engineering of antibody binding sites: Recovery of specific activity in an anti-digoxin single-chain Fv analogue produced in *Escherichia coli*", Proc. Natl. Acad. Sci. USA 85:5879-5883 (1988).
Jaeger et al., "Improved predictions of secondary structures for RNA", Proc. Natl. Acad. Sci. USA 86:7706-10 (1989).
Jaeger et al., "Predicting Optimal and Suboptimal Secondary Structure for RNA", Methods Enzymol. 183:281-306 (1989).
Jameson, et al. The antigenic index: a novel algorithm for predicting antigenic determinants, Comput Appl Biosci 4(1) 181-186 (1988).
Jespers et al., "Guiding the Selection of Human Antibodies from Phage Display Repertoires to a Single Epitope of an Antigen", Biotechnology 12:899, (1994).
Jiang, B. et al., "A Novel Peptide Isolated from a Phage Display Peptide Library with Trastuzumab Can Mimic Antigen Epitope of HER-2", J. Biol. Chem., 280(6):4656-4662 (2005).
Jiang, et al., "TLR9 stimulation drives naive B cells to proliferate and to attain enhanced antigen presenting function", Eur. J. Immunol., 37:2205-2213 (2007).
Jinushi, M. et al. "MHC class I chain-related protein A antibodies and shedding are associated with the progression of multiple myeloma", PNAS, 105:1285-1290 (2008).
Jinushi, M. et al., "Enhancing the clinical activity of granulocyte-macrophage colony stimulating factor-secreting tumor cell vaccines", Immunological Reviews, 222:287-298 (2008).
Johnson et al. A Structural Basis for Sequence Comparisons: An Evaluation of Scoring Methodologies, J. Mol. Biol. 233:716-738 (1993).
Jones, P. et al. "Replacing the complementarity-determining regions in a human antibody with those from a mouse", Nature 321:522-525 (1986).
Jordan, Peter A. et al., "A role for the thiol isomerase protein ERP5 in platelet function," Blood, 105(4):1500-1507 (2005).
Jourdan et al., "An in vitro model of differentiation of memory B cells into plasmablasts and plasma cells including detailed phenotypic and molecular characterization", Blood, 114:5173-5181 (2009).
Kaiser et al., "Disulphide-isomerase-enabled shedding of tumour-associated NKG2D ligands", Nature, 447 (7143):182-486 (2007).

(56) References Cited

OTHER PUBLICATIONS

Kalos M, et al., "T Cells with Chimeric Antigen Receptors Have Potent Antitumor Effects and Can Establish Memory in Patients with Advanced Leukemia", Sci Transl Med. Aug. 10;3 (95), (2011).
Kaneko et al., "Anti-Inflammatory Activity of Immunoglobulin G Resulting from Fc Sialylation", Science 313:670-673 (2006).
Kelland, L.R. "Of mice and men: values and liabilities of the athymic nude mouse model in anticancer drug development", Eur. J Cancer, vol. 40 (6), pp. 827-836 (2004).
Kettleborough et al, "Humanization of a mouse monoclonal antibody by CDR-grafting: the importance of framework residues on loop conformation", Protein Eng 4(7) 773 83 (1991).
Kirkland et al., "Analysis of the Fine Specificity and Cross-Reactivity of Monoclonal Anti-Lipid A Antibodies", J Immunol. 137:3614 (1986).
Klimka, A., et al., "Human anti-CD30 recombinant antibodies by guided phage antibody selection using cell panning," British Journal of Cancer, vol. 83(2), pp. 252-260 (2000).
Klinman "CpG DNA as a vaccine adjuvant", Expert Review Vaccines 2(2):305-15 (2003).
Kostelny et al., "Formation of a Bispecific Antibody by the Use of Leucine Zippers", Journal of Immunol. 148, 1547-1553 (1992).
Kratz et al. "Native display of complete foreign protein domains on the surface of hepatitis B virus capsids", Proc Natl Acad Sci USA. 96(5):1915-1920 (1999).
Krogh et al. "Predicting transmembrane protein topology with a hidden Markov model Application to complete genomes", Journal of Molecular Biology, 305(3) 567-580, (2001).
Kunkel et al., "Plasma-Cell Homing", Nat. Rev. Immunol., 3:822-829 (2003).
Kuo et al.,"Anti-caveolin-1 antibodies as anti-prostate cancer therapeutics," Hybridoma, 31 (2): 77-86 (2012).
Kyte et al. "A Simple Method for Displaying the Hydropathic Character of a Protein", J Mol Biol 157 105-132 (1982).
Lanzavecchia et al., "Human B cell memory", Curr. Opin. Immunol. 21:298-304 (2009).
Leblond et al.,"The amphipathic alpha-helical repeats of apolipoprotein A-I are responsible for binding of high density lipoproteins to HepG2 cells," J. Biol. Chem., 266 (10): 6058-6067 (1991).
Li et al., "Human B cell memory", Nature Biotechnology 24(2):210-215 (2006).
Liu et al. "Perturbation of NK cell peripheral homeostasis accelerates prostate carcinoma metastasis", The Journal of Clinical Investigation 123(10):4410-4422 (2013).
Liu et al.,"The membrane type matrix metalloproteinase MMP14 mediates constitutive shedding of MHC class I chain related molecule A independent of A disintegrin and metalloproteinases," J. Immunol. 184 (7): 3346-3350 (2010).
Liu R. et al. "Monoclonal Antibody against Cell Surface GRP78 as a Novel Agent in Suppressing P13K/AKT Signaling, Tumor Growth, and Metastasis", Clinical Cancer Research, 19(24):6802-6811 (2013).
Lonberg "Human antibodies from transgenic animals", Nature Biotechnology 23(9): 1117-1125, (2005).
Lonberg et al, "Antigen-specific human antibodies from mice comprising four distinct genetic modifications", Nature 368 856-859 (1994).
Lonberg et al, "Human Antibodies from Transgenic Mice", International Reviews of Immunology, 13 65-93 (1995).
MacCallum "Antibody-antigen Interactions: Contact Analysis and Binding Site Topography", J. Mol. Biol, 262, 732-745 (1996).
Makabe et al., "Thermodynamic Consequences of Mutations in Vernier Zone Residues of a Humanized Anti-human Epidermal Growth Factor Receptor Murine Antibody, 528", Journal of Biological Chemistry, 283:1156-1166 (2008).
Marks et al, "By-Passing Immunication: Building High Affinity Human Antibodies by Chain Shuffling", Bio/Technology 10, 779-783 (1992).
Marks et al, "Human Antibodies from V-gene Libraries Displayed on Phage", J Mol Biol, 222 581-597 (1991).
Marten et al., "Soluble MIC is Elevated in the Serum of Patients with Pancreatic Carcinoma Diminishing Gamma Delta T Cell Cytotoxicity," Int J Cancer 119:2359-65 (2006).
Martin, D., et al., "Symposium on Cancer Immunology and Immunotherapy," Roche/Nature Medicine, 91 pages (2011).
McCafferty et al, "Phage antibodies: filamentous phage displaying antibody variable domains", Nature, 348 552-554 (1990).
Mei et al., "Expression of NKG2D ligands in multidrug-resistant nasopharyngeal carcinoma cell line CNE2/DDP and heir effects on cytotoxicity of natural killer cells," Nan Fang Yi Ke Da Xue Xue Bao., 27 (6):887-889 (2007).
Meyers E. et al. "Optimal alignments in linear space", CABIOS, 4:11-17 (1989).
Milone et al. "Chimeric Receptors Containing CD137 Signal Transduction Domains Mediate Enhanced Survival of T Cells and Increased Antileukemic Efficacy In Vivo", Mol. Ther. 17:1453 (2009).
Moldenhauer et al., "Identity of HML-1 Antigen on Intestinal Intraepithelial T Cells and of B-ly7 Antigen on Hairy Cell Leukaemia", Scand. J Immunol. 32:77 (1990).
Moms et al. "Genetically Engineered Antibody Molecules", Advances in Immunology 44 65-92 (1988).
Momson et al. "Chimeric human antibody molecules: Mouse antigen-binding domains with human constant region domains", Proc Natl Acad Sci. USA. 81 6851-685 5 (1984).
Morel et al., "Monoclonal Antibodies to Bovine Serum Albumin: Affinity and Specificity Determinations", Mol. Immunol. 25(1):7 (1988).
Morrison et al, "Chimeric human antibody molecules: Mouse antigen-binding domains with human constant region domains", Proc Natl Acad Sci USA, 81 6851-6855 (1984).
Morrison, "Success in Specification", Nature 368, 812-13 (1994).
Nausch et al., "NKG2D ligands in tumor immunity," Oncogene, 27:5944-5958 (2008).
Nechansky et al., "Compensation of endogenous IgG mediated inhibition of antibody-dependent cellular cytotoxicity by glyco-engineering of therapeutic antibodies", Molecular Immunology 44(7): 1815-1817 (2007).
Needleman et al. "A General Method Applicable to the Search for Similarities in the Amino Acid Sequence of Two Proteins", J. Mol. Biol. 48:443-453 (1970).
Nelson et al., "Cancer cells engineered to secrete granulocyte-macrophage colony-stimulating factor using ex vivo gene transfer as vaccines for the treatment of genitourinary malignancies," Cancer Chemother. Pharmacol., 46 (Suppl.): S67-72 (2000).
Neuberger, "Generating high-avidity human Mabs in mice", Nature Biotechnology 14,826 (1996).
Odendahl et al., "Generation of migratory antigen-specific plasma blasts and mobilization of resident plasma cells in a secondary immune response", Blood, 105:1614-1621 (2005).
Padlan, "A possible procedure for reducing the immunogenicity of antibody variable domains while preserving their ligand-binding properties", Molecular Immunology, 28 489-498 (1991).
Padlan, "Anatomy of the Antibody Molecule", Molecular Immunology 31(3) 169-217 (1994).
Padlan, "X-Ray Crystallography of Antibodies", Advances in Protein Chemistry 49:57-133 (1996).
Pantazes, R.J. et al., "OptCDR: a general computational method for the design of antibody complementarity determining regions for targeting epitope binding," Protein Engineering, Design & Selection, 23(11):849-353 (2010).
Park et al., "Prediction of protein-protein interaction types using association rule based classification", BMC: Bioinformatics, 10:1471-2105 (2009).
Pashine et al. "Targeting the innate immune response with improved vaccine adjuvants", Nature Med. 11(4):S63-S68 (2005).
Pearson et al. "Improved tools for biological sequence comparison", Proc. Natl. Acad. Sci. USA 85:2444 (1988).
Pearson, "Rapid and Sensitive Sequence Comparison with FASTP and FASTA", Meth. Enzymology, 183:63-98 (1990).
Pende et al.,"Major histocompatibility complex class I-related chain A and UL 16-binding protein expression on tumor cell lines of

(56) References Cited

OTHER PUBLICATIONS different histotypes: analysis of tumor susceptibility to NKG2D-dependent natural killer cell cytotoxicity," Cancer Res., 62 (21):6178-6186 (2002).
Pettersen et al., "CD47 signals T cell death," J. Immunol., 162 (12):7031-7040 (1999).
Phumyen, A. et al., "Improved Binding Activity of Antibodies Against Major Histocompatibility Complex Class I Chain Related Gene A by Phage Display Technology for Cancer-Targeted Therapy," Journal of Biomedicine and Biotechnology, vol. 2012(597647) 8 pages, (2012).
Pluckthun, "Mono- and Bivalent Antibody Fragments Produced in *Escherichia coli*: Engineering, Folding and Antigen Binding", Immunol. Reviews 130:151-188 (1992).
Ponsel, Dirk et al., "High Affinity, Developability and Functional Size: The Holy Grail of Combinatorial Antibody Library Generation," Molecules, 16: 3675-3700 (2011).
Queen, C. et al. "A humanized antibody that binds to the interleukin 2 receptor", Proc. Natl. Acad. Sci. USA 86:10029-10033 (1989).
Rader, C. et al., "A Phage Display Approach for Rapid Antibody Humanization: Designed Combinatorial V Gene Libraries," PNAS, USA, vol. 95, pp. 8910-8915 (1998).
Riechmann, L. et al. "Reshaping human antibodies for therapy", Nature 332:323-327 (1998).
Riemer, A. et al. "Matching of trastuzumab (Herceptin) epitope mimics onto the surface of Her-2/neu—a new method of epitope definition", Mol. Immunol, 42:1121-1124 (2005).
Rudikoff, S. et al., "Single amino acid substitution altering antigen-binding specificity," Proc Natl Acad Sci USA, 79:1979-1983 (1982).
Saijo, N., "What are the reasons for negative phase III trials of molecular-target-based drugs?", Cancer Sci., 95 (10):772-776 (2004).
Salih, Helmut R. et al., "Cutting Edge: Down-Regulation of MICA on Human Tumors by Proteolytic Shedding," The Journal of Immunology, 169:4098-4102 (2002).
Salih, Helmut R. et al., "Functional expression and release of ligands for the activating immunoreceptor NKG2D in Leukemia," Blood, 102(4):1389-1396 (2003).
Sarmay et al. "Mapping and Comparison of the Interaction Sites on the Fc Region of IgG Responsible for Triggering Antibody Dependent Cellular Cytotoxicity (ADCC) through Different Types of Human Fcy Receptor", Molec. Immunol. 29 (5): 633-9 (1992).
Scallon et al., "Higher levels of sialylated Fc glycans in immunoglobulin G molecules can adversely impact functionality", Mol Immunol. 44(7): 1524-34 (2007).
Scatchard, "The attractions of proteins for small molecules and ions", Ann NY Acad Sci 51 660-672, (1949).
Scheid et al., "Broad diversity of neutralizing antibodies isolated from memory B cells in HIV-infected individuals", Nature, 458:636-640 (2009).
Schoenfeld J. et al., "Active Immunotherapy Induces Antibody Responses That Target Tumor Angiogenesis," Microenvironment and Immunology, Cancer Research, 70(24):10150-10160 (2010).
Shields, R.L. et al. "High Resolution Mapping of the Binding Site on Human IgG1 for FcgRI, FcgRII, FcgRIII, and FcRn and Design of IgG1 Variants with Improved Binding to the FcgR", J Biol. Chem. 276:6591-6604 (2001).
Shields, R.L. et al. "Lack of Fucose on Human IgG1 N-Linked Oligosaccharide Improves Binding to Human FcyRIII and Antibody-dependent Cellular Toxicity", J Biol. Chem. 277:26733-26740 (2002).
Sircar, A. et al., "Rosetta Antibody: antibody variable region homology modeling server," Nucleic Acids Research, vol. 37, pp. W474-W479 (2009).
Skerra et al., "Bacterial expression of immunoglobulin fragments", Curr. Opinion in Immunol., 5:256-262 (1993).
Smith et al. "Comparison of Biosequences", Advances in Applied Mathematics, 2:482 (1981).
Songsivilai et al. "Bispecific antibody: a tool for diagnosis and treatment of disease", Clin. Exp. Immunol. 79:315-321 (1990).
Stahli et al.,"Distinction of Epitopes by Monoclonal Antibodies", Methods in Enzymology 92:242-253 (1983).
Steinle, A. et al., "Diversification, expression, and gammadelta T cell recognition of evolutionarily distant members of the MIC family of major histocompatibility complex class I-related molecules," Proc. Natl. Acad. Sci. USA, vol. 95, pp. 12510-12515 (1998).
Strohl, "Optimization of Fc-mediated effector functions of monoclonal Antibodies", Current Opinion in Biotechnology 20:685-691 (2009).
Suarez-Alvarez, B. et al., "Identification of epitopes and immunodominant regions on the MICA protein defined by alloantibodies from kidney transplant patients," Transplantation, Williams and Wilkins, GB, 88 (3) Suppl, p. S68-S77 (2009).
Tang, B. et al., "Evaluation of human major histocompatibility complex class I chain-related A as a potential target for tumor imaging," Cancer Letters, New York, NY, US, vol. 263 (1), pp. 99-106 (Jan. 30, 2008).
Tao et al. "Role of Carbohydrate in the Structure and Effector Functions Mediated by the Human IgG Constant Region", J. Immunol. 143:2595-2601 (1989).
Tao et al., "Structural Features of Human Immunoglobulin G that Determine Isotype-specitic Differences in Complement Activation", J. Exp. Med. 178:661 (1993).
Taylor, The Classification of Amino Acid Conservation, J. Theor. Biol. 119:205-218 (1986).
Thom, George et al., "Probing a protein-protein interaction by in vitro evolution," PNAS, vol. 103(20):7619-7624 (2006).
Tomlinson, I. M., et al. "The Repertoire of Human Germline VH Sequences Reveals about Fifty Groups of VH Segments with Different Hypervariable Loops" J. Mol. Biol. 227:776-798 (1992).
Umana et al. "Engineered glycoforms of an antineuroblastoma IgG1 with optimized antibodydependent cellular cytotoxic activity", Nat. Biotech. 17:176-180 (1999).
Vajdos, FF et al., "Comprehensive functional maps of the antigen-binding site of an anti-ErbB2 antibody obtained with shotgun scanning mutagenesis," J Mol Biol. 320(2):415-428 (2002).
Verhoeyen et al, "Reshaping Human Antibodies: Grafting an Antilysozyme Activity", Science 239 1534 1536 (1988).
Vitetta, Ellen S. et al., "Monoclonal Antibodies as Agonists: An Expanded Role for Their Use in Cancer Therapy," Cancer Research, 54:5301-5309 (1994).
Wang et al. "Role of the Unfolded Protein Response Regulator GRP78/BiP in Development, Cancer, and Neurological Disorders", Antioxidants and Redox Signaling 11(9): 2307-2316 (2009).
Wang et al., "Human immunoglobulin variable region gene analysis by single cell RT-PCR", J. Immunol. Methods, 244:217-225 (2000).
Ward et al., "Binding activities of a repertoire of single immunoglobulin variable domains secreted from *Escherichia coli*", Nature 341:544-546 (1989).
Weber, "Review: anti-CTLA-4 antibody ipilimumab: case studies of clinical response and immune-related advers events," Oncologist, 12(7): 864-872 (2007).
Whiteside, T. et al., "Antigen-Processing Machinery in Human Dendritic Cells; Up-regulation by Maturation and Down-Regulation by Tumor Cells," J Immunol., vol. 173, pp. 1526-1534 (2004).
Wongsena et al "Production and characterization of monoclonal antibodies against major histocompatibility complex class 1 chain-related gene A," Tissue Antigens, 72(5):431-440 (2008).
Wu et al., "Prevalent Expression of the Immunostimulatory MHC Class I Chain-related Molecule is Counteracted by Shedding in Prostate Cancer," J Clin Invest 114: 560-8 (2004).
Wu et al., "Rational Design of Envelope Identifies Broadly Neutralizing Human Monoclonal Antibodies to HIV-1", Science, 329:856-861 (2010).
Yeung et al., "Engineering Human IgG1 Affinity to Human Neonatal Fc Receptor: Impact of Affinity Improvement on Pharmacokinetics in Primates", J Immunol, 182:7663-7671 (2010).
Yoshida et al., "Memory B and memory plasma Cells", Immunol. Rev., 237:117-139 (2010).
Yu et al. "Minimal Lipidation Stabilizes Protein-Like Molecular Architecture", J Am. Chem. Soc., 120(39):9979-9987 (1998).

(56) References Cited

OTHER PUBLICATIONS

Zapata et al, "Engineering linear F(ab')2 fragments for efficient production in *Escherichia coli* and enhanced antiproliferative activity", Protein Eng 8(10) 1057-1062 (1995).
Zou, Yizhou et al., "MICA is a Target for Complement-Dependent Cytotoxicity With Mouse Monoclonal Antibodies and Human Alloantibodies," Human Immunology, 63:30-39 (2002).
Zuker, "On Finding All Suboptimal Foldings of an RNA Molecule", Science 244:48-52 (1989).
Zwirner, N. et al., "Immunobiology of the human AMC class I chain-related gene A (MICA): from transplantation immunology to tumor immune escape," Immunologia, 25(1):25-38 (2006).
Morrison et al., "Genetically Engineered Antibody Molecules", Advances in Immunology, vol. 44, p. 65-92 (1988).
Spear et al., "NKG2D ligands as therapeutic targets", Cancer Immunity, vol. 13, p. 1-14 (May 1, 2013).
Wang, X. et al., "An six-amino acid motif in the α3 domain of MICA is the cancer therapeutic target to inhibit shedding," Biochemical and Biophysical Research Communications, 387:476-481 (2009).

* cited by examiner

Figure 2A

CM3332 Ab4 CM3332 Ab28 CM3332 Ab29

```
Majority   HADCLQELRRYLKSGVVLRRTVPPMVNVTRSEASEGNITVTCRASGFYPWNITLSWRQDGVSLSHDTQQWGDVLPDGNGT
                   170       180       190       200       210       220       230       238
MICA009.seq HADCLQELRRYLESSVVLRRTVPPMVNVTRSEASEGNITVTCRASSFYPRNITLTWRQDGVSLSHDTQQWGDVLPDGNGT 238
MICA015.seq HADCLQELRRYLKSGVVLRRTVPPMVNVTRSEASEGNITVTCRASGFYPWNITLSWRQDGVSLSHDTQQWGDVLPDGNGT 238
MICA004.seq HADCLQELRRYLESSVVLRRRVPPMVNVTRSEASEGNITVTCRASSFYPRNITLTWRQDGVSLSHDTQQWGDVLPDGNGT 238
MICA018.seq HADCLQELRRYLKSGVVLRRTVPPMVNVTRSEASEGNITVTCRASGFYPWNITLSWRQDGVSLSHDTQQWGDVLPDGNGT 238
MICA017.seq HADCLQELRRYLKSGVVLRRTVPPMVNVTRSEASEGNITVTCRASGFYPWNITLSWRQDGVSLSHDTQQWGDVLPDGNGT 238
MICA012.seq HADCLQELRRYLKSGVVLRRTVPPMVNVTRSEASEGNITVTCRASGFYPWNITLSWRQDGVSLSHDTQQWGDVLPDGNGT 238
MICA010.seq HADCLQELRRYLESSVVLRRTVPPMVNVTRSEASEGNITVTCRASSFYPRNIILTWRQDGVSLSHDTQQWGDVLPDGNGT 238
MICA001.seq HADCLQELRRYLKSGVVLRRTVPPMVNVTRSEASEGNITVTCRASGFYPWNITLSWRQDGVSLSHDTQQWGDVLPDGNGT 238
MICA007.seq HADCLQELRRYLKSGVVLRRTVPPMVNVTRSEASEGNITVTCRASGFYPWNITLSWRQDGVSLSHDTQQWGDVLPDGNGT 238
MICA002.seq HADCLQELRRYLKSGVVLRRTVPPMVNVTRSEASEGNITVTCRASGFYPWNITLSWRQDGVSLSHDTQQWGDVLPDGNGT 238
MICA008.seq HADCLQELRRYLESGVVLRRTVPPMVNVTRSEASEGNITVTCRASSFYPRNIILTWRQDGVSLSHDTQQWGDVLPDGNGT 238

Majority   YQTWVATRICQGEEQRFTCYMEHSGNHSTHPVPSGK
           240       250       260       270
MICA009.seq YQTWVATRICQGEEQRFTCYMEHSGNHSTHPVPSGK 274
MICA015.seq YQTWVATRICQGEEQRFTCYMEHSGNHSTHPVPSGK 274
MICA004.seq YQTWVATRICQGEEQRFTCYMEHSGNHSTHPVPSGK 274
MICA018.seq YQTWVATRICQGEEQRFTCYMEHSGNHSTHPVPSGK 274
MICA017.seq YQTWVATRICQGEEQRFTCYMEHSGNHSTHPVPSGK 274
MICA012.seq YQTWVATRICQGEEQRFTCYMEHSGNHSTHPVPSGK 274
MICA010.seq YQTWVATRICRGEEQRFTCYMEHSGNHSTHPVPSGK 274
MICA001.seq YQTWVATRICQGEEQRFTCYMEHSGNHSTHPVPSGK 274
MICA007.seq YQTWVATRICQGEEQRFTCYMEHSGNHSTHPVPSGK 274
MICA002.seq YQTWVATRICQGEEQRFTCYMEHSGNHSTHPVPSGK 274
MICA008.seq YQTWVATRICRGEEQRFTCYMEHSGNHSTHPVPSGK 274
```

Ameneded

Ameneded

Figure 5: Therapeutic activity of human anti-MICA antibodies
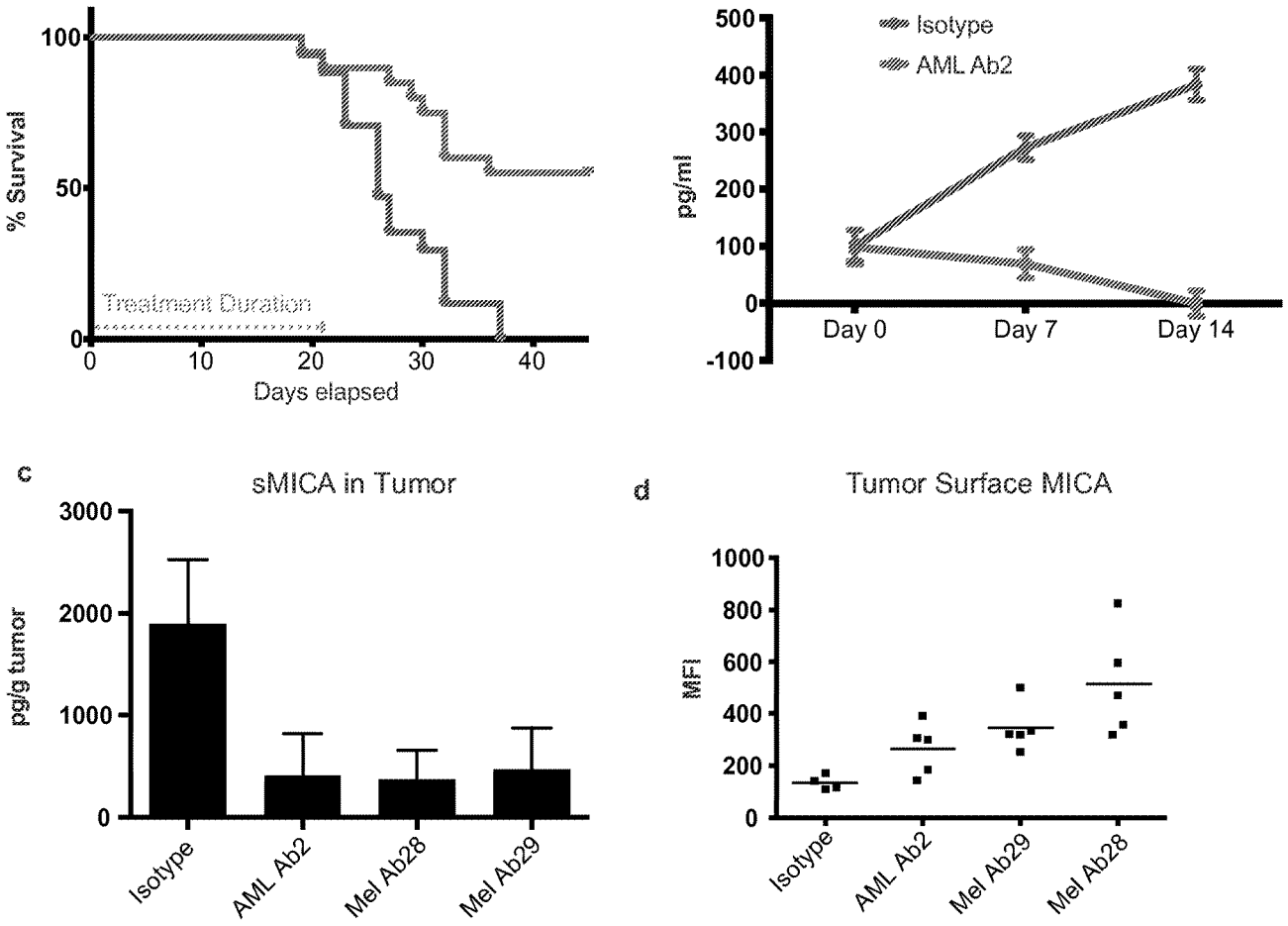

Figure 6: Human antibodies enhance NK cell accumulation and function in tumors
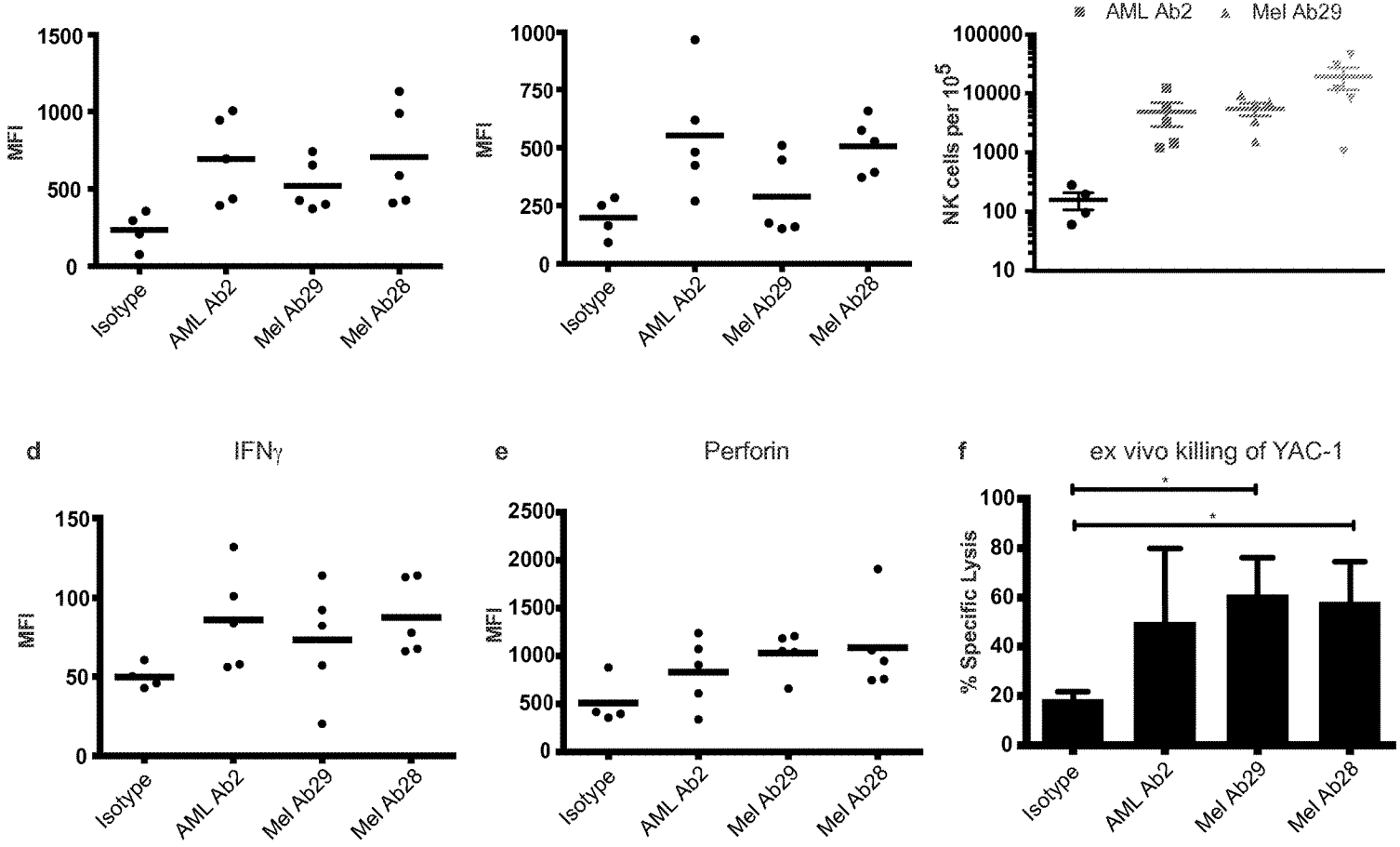

VACCINE COMPOSITIONS AND METHODS FOR RESTORING NKG2D PATHWAY FUNCTION AGAINST CANCERS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application *is a reissue of U.S. Pat. No. 10,279,021, issued May 7, 2019, which* is the National Stage of International Application No. PCT/US2015/020694, filed Mar. 16, 2015, which claims priority to, and the benefit of U.S.S.N. 61/953,064 filed on Mar. 14, 2014, the contents of each of which are incorporated herein by reference in their entirety.

GOVERNMENT SUPPORT

This invention was made with Government support under Grant No. NCI 1R01CA173750-01, awarded by the National Institutes of Health. The Government has certain rights in the invention.

INCORPORATION OF SEQUENCE LISTING

The contents of the text file submitted electronically herewith are incorporated herein by reference in their entirety: A computer readable format copy of the Sequence Listing (filename: DFCI_082_N01US_SeqList_ST25.txt, date recorded: Sep. 13, 2016, file size 34.6 kb).

TECHNICAL FIELD

This invention relates to methods and compositions for inducing an anti-cancer immune response in a human subject.

BACKGROUND

MICA is a ligand for NKG2D, a C-type lectin-like, type II transmembrane receptor expressed on most human NK cells, γδ T cells, and CD8+ T cells. Upon ligation, NKG2D signals through the adaptor protein DAP10 to evoke perforin dependent cytolysis and to provide co-stimulation. In humans, the NKG2D ligands include MHC class I chain-related protein A (MICA), the closely related MICB, UL-16 binding proteins (ULBP) 1-4, and RAE-1G.

While NKG2D ligands are not usually found on healthy tissues, various forms of cellular stress, including DNA damage, may upregulate ligand expression, resulting in their frequent detection in multiple solid and hematologic malignancies, including melanoma. NKG2D activation through ligand positive transformed cells contributes to extrinsic tumor immunity, since NKG2D deficient mice manifest enhanced tumor susceptibility. But in many cancer patients NKG2D-mediated tumor immunity is ineffective. In part, immune escape may be achieved by the shedding of NKG2D ligands from tumor cells, which triggers internalization of surface NKG2D and impaired function of cytotoxic lymphocytes. See e.g., Wu et al., "Prevalent Expression of the Immunostimulatory MHC Class I Chain-related Molecule is Counteracted by Shedding in Prostate Cancer," J Clin Invest 114: 560-8 (2004); Groh et al., "Tumour-derived Soluble MIC Ligands Impair Expression of NKG2D and T-cell Activation," Nature 419: 734-8 (2002); Doubrovina et al., "Evasion from NK Cell Immunity by MHC Class I Chain-related Molecules Expressing Colon Adenocarcinoma," J Immunol 171:6891-9 (2003). A reduction in the density of MIC expressed on the tumor cell surface due to MIC shedding from tumors is also one of the mechanisms for tumor evasion. See Marten et al., "Soluble MIC is Elevated in the Serum of Patients with Pancreatic Carcinoma Diminishing Gamma Delta T Cell Cytotoxicity," Int J Cancer 119:2359-65 (2006). Soluble NKG2D ligands may also stimulate the expansion of regulatory NKG2D+CD4+ Foxp3− T cells that may antagonize anti-tumor cytotoxicity through Fas ligand, IL-10, and TGF-β.

MICA is a NKG2D ligand shed from tumor cells, i.e., released from the cell surface into the surrounding medium, and sera from a subset of cancer patients contains elevated levels of the soluble form (sMICA). MIC (the term "MIC" referring to MICA and MICB) shedding is accomplished in part through interactions with the protein disulfide isomerase ERp5, which cleaves a disulfide bond in the MIC α3 domain, rendering it susceptible to proteolysis by ADAM-10/17 and MMP14. Methods of treating cancer by administering anti-MIC antibodies or antigen-binding peptide fragments have been described. For example, U.S. Pat. No. 8,182,809 describes such methods utilizing a purified antibody or a polypeptide comprising an antigen-binding fragment thereof that specifically binds to the amino acid sequence NGTYQT located in the α3 ectodomain of the MIC polypeptide, such that the interaction of the MIC polypeptide and ERp5 is inhibited and the shedding of MIC is inhibited. And U.S. Pat. No. 7,959,916 describes methods of inhibiting the shedding of MIC polypeptides from cancer cells using anti-MIC α3 domain antibodies. Tumor-derived soluble MIC polypeptides, either MICA or MICB, or both, have also been suggested as biomarkers for diagnosis and prognosis of cancer and anti-MICA or anti-MICB antibodies as therapeutic agents for the treatment of cancer and autoimmune diseases. For example, U.S. Pat. No. 7,771,718 describes methods of relieving MIC-induced suppression of NKG2D in lymphocytes using anti-MIC antibodies to bind soluble MIC polypeptides.

In practice, methods of treating cancer or other diseases with therapeutic antibodies is relatively expensive because of the need to produce large quantities of such antibodies of sufficient purity for infusion to patients. In view of the complexity of large-scale antibody production and the specialized requirements for antibody infusion protocols, alternative methods are needed to target MIC polypeptides in a more efficient and cost-effective manner. The present invention provides a solution to this problem by providing vaccines for the induction of anti-MIC antibodies in a subject.

Tumor vaccines are typically composed of tumor antigens and immunostimulatory molecules (e.g. cytokines or TLR ligands) that work together to induce antigen-specific cytotoxic T cells (CTLs) that recognize and lyse tumor cells. At this time, almost all vaccines contain either shared tumor antigens or whole tumor cell preparations (Gilboa, 1999). The shared tumor antigens are immunogenic proteins with selective expression in tumors across many individuals and are commonly delivered to patients as synthetic peptides or recombinant proteins (Boon et al., 2006). In contrast, whole tumor cell preparations are delivered to patients as autologous irradiated cells, cell lysates, cell fusions, heat-shock protein preparations or total mRNA (Parmiani et al., 2007). Since whole tumor cells are isolated from the patient, the cells express patient-specific tumor antigens as well as shared tumor antigens. Finally, there is a third class of tumor antigens that has rarely been used in vaccines due to technical difficulties in identifying them (Sensi et al. 2006). This class consists of proteins with tumor-specific mutations that result in altered amino acid sequences. Such mutated proteins have the potential to: (a) uniquely mark a tumor (relative to non-tumor cells) for recognition and destruction by the immune system (Lennerz et al., 2005); (b) avoid central and sometimes peripheral T cell tolerance, and thus be recognized by more effective, high avidity T cells receptors (Gotter et al., 2004).

SUMMARY

The present invention provides compositions and methods for treating cancer in a subject by eliciting an immune response against a MIC polypeptide. The term "MIC" as used herein refers to MICA and/or MICB. In one embodiment, the invention provides a vaccine composition for treating cancer, the composition comprising, as an immunogenic component, an effective amount of a peptide comprising or consisting of one or more of SEQ ID NOs 1-23, the effective amount being an amount effective to elicit an immune response against a MIC polypeptide, or the cancer. In another embodiment, the vaccine composition comprises as an immunogenic component, an effective amount of a peptide comprising or consisting of one or more of SEQ ID NOs 1-4 or 2-4, one or more of SEQ ID NOs 5-7, one or more of SEQ ID NOs 8-10, or one or more of SEQ ID NOs 5-13. In another embodiment, the vaccine composition comprises as an immunogenic component, an effective amount of a peptide comprising or consisting of one or more of SEQ ID NOs 14-23, one or more of SEQ ID NOs 15-23, one or more of SEQ ID NOs 18-23, or one or more of SEQ ID NOs 21-23.

In one embodiment, the vaccine composition is effective to elicit an in vitro immune response against a MIC polypeptide. In another embodiment, the vaccine composition is effective to elicit an in vivo immune response against a MIC polypeptide.

In one embodiment, the immune response is directed against a MIC polypeptide that is not attached to a cell, also referred to as a soluble MIC polypeptide. The soluble MIC may be in either a monomeric or multimeric form. In another embodiment, the immune response is directed against a cancer cell expressing a MIC polypeptide. The cancer cell may be in vitro or in vivo. In one embodiment, the vaccine composition is effective to elicit an immune response against a cancer cell expressing a MIC polypeptide. The cancer cell may be in vitro or in vivo.

In one embodiment, the MIC polypeptide is a MICA or MICB polypeptide, or a fusion protein containing the α3 domains of MICA and MICB.

Any cancer cell expressing MIC can be treated using the compositions and methods of the invention. In one embodiment, the cancer is selected from the group consisting of prostate cancer, multiple myeloma, gliobastoma multiforme, and melanoma. In one embodiment, the cancer is melanoma.

In one embodiment, the peptide comprises or consists of one or more of SEQ ID NOs 8-13, or a peptide having 90% or 95% amino acid sequence identity to any one of the same. In one embodiment, the peptide comprises or consists of one or more of SEQ ID NOs 15-23, or a peptide having 90% or 95% amino acid sequence identity to any one of the same.

In one embodiment, the vaccine composition comprises a plurality of peptides selected from two or more of SEQ ID NOs 5-10, or a peptide having 95% amino acid sequence identity to any of the same; or from two or more of SEQ ID NOs 8-13, or a peptide having 90% amino acid sequence identity to any of the same. In one embodiment, the vaccine composition comprises a plurality of peptides selected from two or more of SEQ ID NOs 15-20, or a peptide having 95% amino acid sequence identity to any of the same; or from two or more of SEQ ID NOs 21-23, or a peptide having 90% amino acid sequence identity to any of the same.

In one embodiment, the peptide is conjugated to a carrier protein. In one embodiment, the carrier protein is selected from tetanus toxin and diphtheria toxin.

In one embodiment, the vaccine composition comprises a viral capsid protein engineered to display the at least one peptide or plurality of peptides on its surface. In one embodiment, the viral capsid protein is a hepatitis B capsid protein.

In one embodiment, the vaccine composition is in the form of a polymer scaffold comprising the at least one peptide or a plurality of peptides. In one embodiment, the polymer scaffold is a porous, poly-lactide-co-glycolide (PLG) polymer scaffold. In one embodiment, the polymer scaffold further comprises one or both of a GM-CSF protein and a Toll-like receptor agonist. In one embodiment, the polymer scaffold further comprises autologous tumor cell lysates of a subject to be treated for cancer with the composition.

The present invention also provides methods of treating cancer in a subject by administering to a subject a vaccine composition described herein. In one embodiment, a vaccine composition of the invention is administered as part of a therapeutic regimen. In one embodiment, the therapeutic regimen further comprises one or more of radiation therapy, immunotherapy, chemotherapy, or targeted therapy. In one embodiment, the methods comprise administering at least two, preferably three separate vaccine compositions of the invention as part of a prime-boost strategy, each vaccine composition having a different immunogen from the others.

Other features and advantages of the invention will be apparent from the following detailed description and figures, and from the claims.

DESCRIPTION OF DRAWINGS

FIGS. 2A and 2B| Epitope conservation among common MICA and MICB alleles. *FIG. 2A shows MICA alleles: MICA009* (*SEQ ID NO 24*), *MICA015* (*SEQ ID NO 25*), *MICA004* (*SEQ ID NO 26*), *MICA018* (*SEQ ID NO 27*), *MICA017* (*SEQ ID NO 28*), *MICA012* (*SEQ ID NO 29*), *MICA010* (*SEQ ID NO 30*), *MICA001* (*SEQ ID NO 31*), *MICA007* (*SEQ ID NO 32*), *MICA002* (*SEQ ID NO 33*), *MICA008* (*SEQ ID NO 34*). *FIG. 2B shows MICB alleles: MICB 001, MICB 002:01:01, MICB 002:01:02, MICB 004:01:01, MICB 004:01:02, MICB 005:01, MICB 005:02:01, MICB 005:02:02, MICB 005:02:03, MICB 005:02:04, MICB 005:03, MICB 005:04, MICB 005:05, MICB 005:06, MICB 005:07, MICB 005:08, MICB 008, MICB 009N, MICB 010, MICB 011, MICB 012 and MICB 18* (*SEQ ID NO 35*); *MICB 003* (*SEQ ID NO 36*), *MICB 006* (*SEQ ID*

Figure 1:
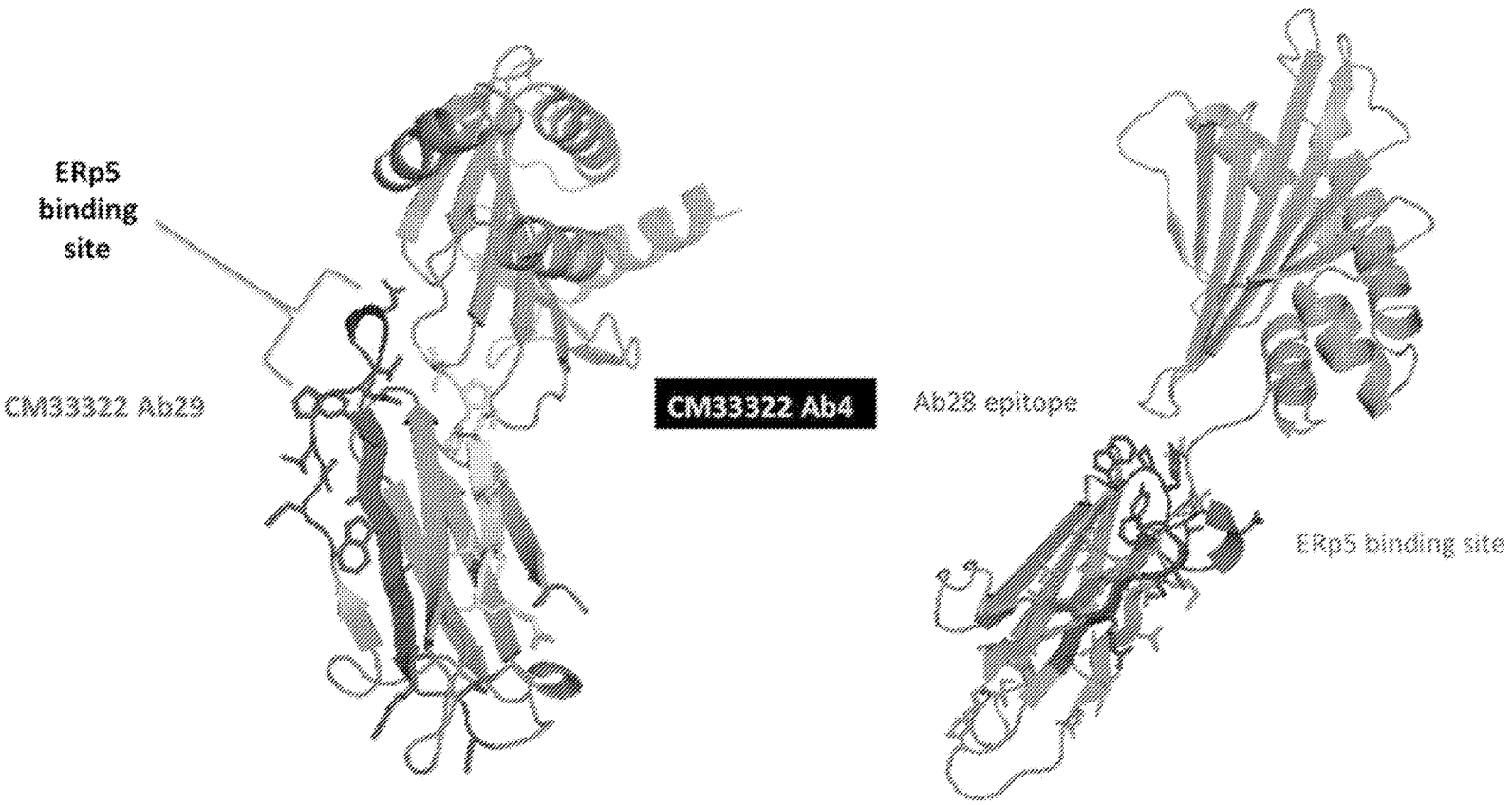
FIG. 1| Mapping of epitopes on MICA*100 reference structure. Epitope mapping was performed using overlapping peptide arrays. Each peptide was a 20 amino acid linear sequence with a 10 amino acid offset for each peptide.
Figure 2B:
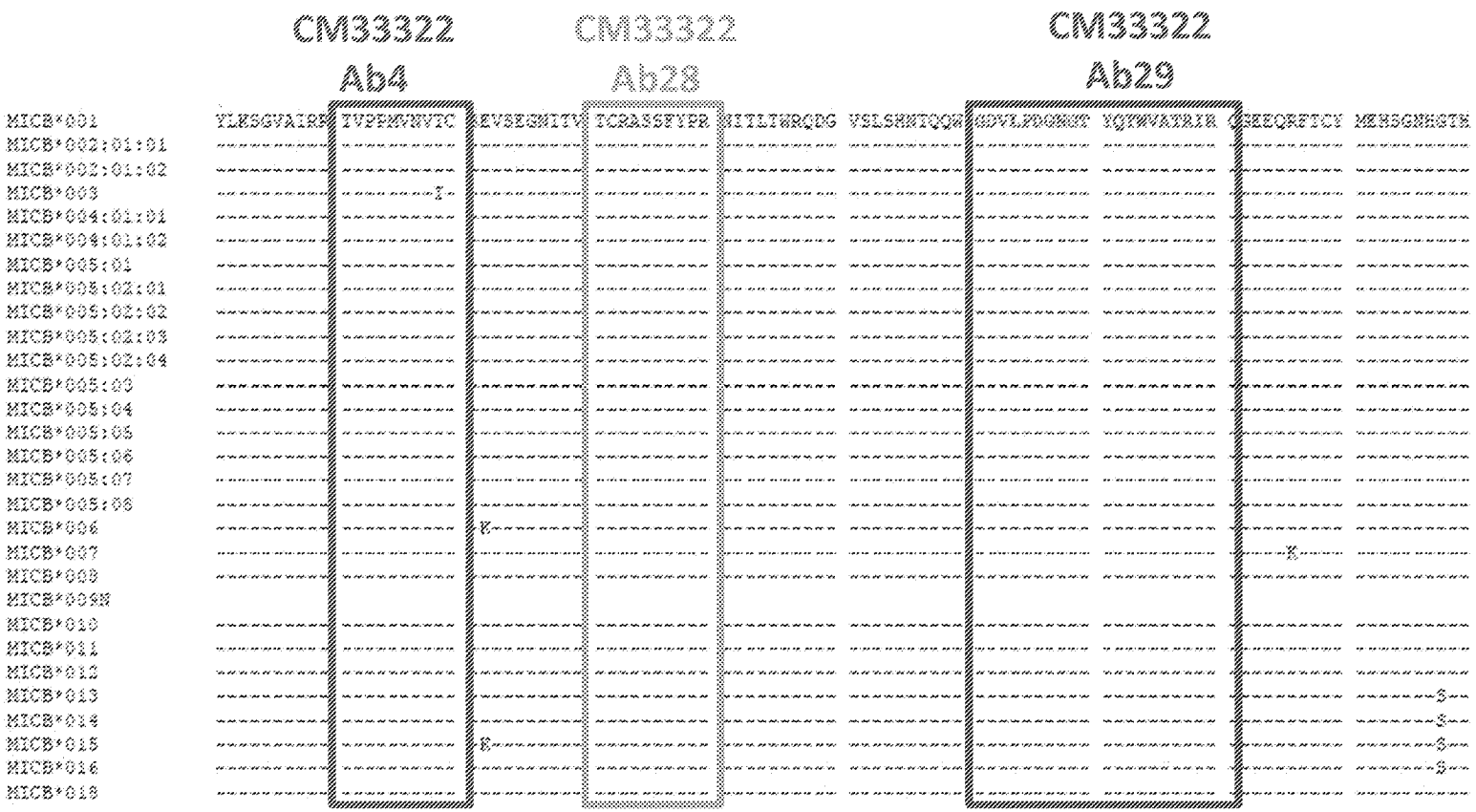

*NO 37), MICB 007 (SEQ ID NO 38); MICB 013, MICB 014 and MICB 016 (SEQ ID NO 39); and MICB 015 (SEQ ID NO 40).*

FIGS. 3A and 3B| Design of chimeric protein with properly placed epitopes for MIC antibodies. The epitopes of MICA Abs 28 and 29 (highlighted in blue and red) were placed into an unrelated protein with a similar Ig domain structure, human CMV protein UL18. Comparison of the structures of MICA a3 (A) and the chimeric protein (B) demonstrates conservation of the epitopes for MICA antibodies 28 and 29.

FIG. 3C| The sequence of the chimeric protein (*SEQ ID NO 42*) is aligned with MICA (*SEQ ID NO 43*) and UL18 sequences (*SEQ ID NO 44*) (C). Residues of UL18 that bind to human LIR were mutated (indicated in white). Residues 206 and 210 of MICA are polymorphic (G/S and W/R, respectively).

FIGS. 4A and 4B| Design of disulfide-stabilized mini-MICA for display of MICA epitopes. A mini-MICA protein was designed to focus B cell responses on critical parts of the protein. A disulfide bond (green) was introduced to stabilize the conformation of the MICA Ab29 epitope. The beta strand connecting Ab28 and Ab29 epitope was deleted to reduce protein flexibility and improve solubility. Note that the N and C termini of the Mini-MICA protein are in close vicinity, which enables display on the surface of the hepatitis B core capsid. Blue—Ab28 epitope, Red—Ab29 epitope.

FIG. 4C| The sequence of mini-MICA (*SEQ ID NO 45*) is aligned with MICA (*SEQ NO 43*).

FIGS. 5A-5D are a series of graphs that depict the therapeutic activity of human anti-MICA antibodies. FIG. 5A is a graph that indicates that the AML Ab2 improved survival of SCID mice implanted with human U937 tumor cells (3×100 μg Ab per week). The amount of days elapsed is indicated on the x-axis, and the percent survival is indicated on the y-axis. FIG. 5B is a graph that depicts that antibody treatment significantly reduced sMICA concentration in the serum of treated mice as measured by ELISA. Treatment duration is indicated on the x-axis, and the concentration of sMICA in the serum is indicated on the y-axis. FIGS. 5C and 5D indicate that following one week of treatment, MICA antibodies reduced sMICA in tumor homogenate (normalized to tumor mass; see FIG. 5C) and increased MICA expression on the surface of tumor cells, as assayed by flow cytometry (see FIG. 5D). The x-axis in FIG. 5C indicates experimental conditions, and the y-axis indicates concentration of sMICA in tumor homagenate. The x-axis in FIG. 5D indicates experimental condition, and the y-axis indicates mean fluorescence intensity (MFI).

FIGS. 6A-6F are a series of graphs that indicate human antibodies enhance NK cell accumulation and function in tumors. For these data, SCID mice bearing U937 tumors were treated for one week with MICA mAbs (3×100 μg) and NK cell function was assessed. FIGS. 6A, 6B, and 6C demonstrate that Antibody treatment increased surface levels of NKG2D (see FIG. 6A) and NKp46 (see FIG. 6B) by tumor infiltrating $CD45^+$ $NK1.1^+$ NK cells and induced NK cell accumulation in tumors (see FIG. 6C, normalized to $1\times10^5$ $CD45^+$ cells). FIGS. 6D and 6E demonstrate that treatment increased IFNγ (see FIG. 6D) and perforin (see FIG. 6E) expression by tumor infiltrating $CD45^+$ $NK.1^+$ NK cells. FIG. 6F depicts that all three human MICA antibodies enhanced ex vivo killing of $^{51}Cr$ labeled YAC-1 cells by splenocytes.

DETAILED DESCRIPTION

The present invention provides compositions and methods for treating cancer in a subject by eliciting an immune response against MIC polypeptides. The terms "elicit," "stimulate," and "induce" are used interchangeably to denote the generation of a de novo immune response in a subject or to denote the enhancement of the strength or persistence of an existing immune response. The compositions of the invention contain, as an immunogenic component (also referred to herein as an "immunogen"), at least one MIC peptide which comprises or consists of the full-length alpha 3 domain of MICA [SEQ ID NO: 1] or MICB [SEQ ID NO: 14]. In certain embodiments, the MIC peptide is an epitope selected from the group consisting of SEQ ID NOs 2-13 or SEQ ID NOs: 15-23.

In the context of the invention, an epitope is a portion of an antigenic molecule capable of eliciting an immune response to the molecule, preferably a cytotoxic T cell response or an antibody-secreting B cell mediated response, or which can be bound by an antibody. The minimal epitopes represented by SEQ ID NOs: 11-13 and 21-23 were identified by the inventors as the antibody-binding epitopes for the CM33322 Ab4, CM33322 Ab28, and CM33322 Ab29, which are described in U.S. Provisional Application Nos. 61/792,034 and 61/913,198 and in U.S. application Ser. No. 14/025,573. These antibodies were isolated from cancer patients responsive to immunotherapy. These antibodies enhance the activity of NK cells and CD8 T cells against cancer cells by inhibiting cleavage of MIC proteins from cancer cells. The antibodies bind to the α3 domain of MIC proteins and have strong anti-tumor activity in relevant animal models. These clinical immunological studies evidence that induction of antibodies against the α3 domain of MIC proteins restores anti-tumor immune function against cancers. In accordance with the present invention, the epitopes recognized by these antibodies can be used as the immunogenic component of a cancer vaccine to stimulate antibody production against the MIC α3 domain. An important element of this invention is that antibodies are produced against the MIC α3 domain, but not against the α1-α2 domains of MIC, given that the NKG2D receptor on NK cells and CD8 T cells binds to the α1-α2 domains. Accordingly, the invention provides the epitopes of the MICA and B proteins that are important for an effective anti-MIC immune response in humans and methods and compositions relating to the use of same as the immunogenic components of a cancer vaccine.

TABLE 1

Location of antibody binding epitopes within the amino acid sequence of MICA*001 reference sequence (SEQ ID NO: 1). Epitopes are in bold and underlined.

| | |
|---|---|
| CM33322 Ab4 (SEQ ID NO: 1) | HSLRYNLTVLSWDGSVQSGFLAEVHLDGQPF LRYDRQKCRAKPQGQWAEDVLGNKTWDRETR DLTGNGKDLRMTLAHIKDQKEGLHSLQEIRV CEIHEDNSTRSSQHFYYDGELFLSQNVETEE WTVPQSSRAQTLAMNVRNFLKEDAMKTKTHY HAMHADCLQELRRYLESSVVLRR**TVPPMVNV TR**SEASEGNITVTCRASSFYPRNITLTWRQD GVSLSHDTQQWGDVLPDGNGTYQTWVATRIC QGEEQRFTCYMEHSGNHSTHPVPSGKVLVLQ SHWQTFHVSAVAAAAAAIFVIIIFYVRCCKK KTSAAEGPELVSLQVLDQHPVGTSDHRDATQ LGFQPLMSALGSTGSTEGA |
| CM33322 Ab28 (SEQ ID NO: 1) | HSLRYNLTVLSWDGSVQSGFLAEVHLDGQPF LRYDRQKCRAKPQGQWAEDVLGNKTWDRETR DLTGNGKDLRMTLAHIKDQKEGLHSLQEIRV CEIHEDNSTRSSQHFYYDGELFLSQNVETEE WTVPQSSRAQTLAMNVRNFLKEDAMKTKTHY HAMHADCLQELRRYLESSVVLRRTVPPMVNV |

TABLE 1-continued

| Location of antibody binding epitopes within the amino acid sequence of MICA*001 reference sequence (SEQ ID NO: 1). Epitopes are in bold and underlined. | |
|---|---|
| | TRSEASEGNITV**TCRASSFYPR**NITLTWRQD<br>GVSLSHDTQQWGDVLPDGNGTYQTWVATRIC<br>QGEEQRFTCYMEHSGNHSTHPVPSGKVLVLQ<br>SHWQTFHVSAVAAAAAAIFVIIIFYVRCCKK<br>KTSAAEGPELVSLQVLDQHPVGTSDHRDATQ<br>LGFQPLMSALGSTGSTEGA |
| CM33322 Ab29<br>(SEQ ID NO: 1) | HSLRYNLTVLSWDGSVQSGFLAEVHLDGQPF<br>LRYDRQKCRAKPQGQWAEDVLGNKTWDRETR<br>DLTGNGKDLRMTLAHIKDQKEGLHSLQEIRV<br>CEIHEDNSTRSSQHFYYDGELFLSQNVETEE<br>WTVPQSSRAQTLAMNVRNFLKEDAMKTKTHY<br>HAMHADCLQELRRYLESSVVLRRTVPPMVNV<br>TRSEASEGNITVTCRASSFYPRNITLTWRQD<br>GVSLSHDTQQW**GDVLPDGNGTYQTWVATRIC**<br>QGEEQRFTCYMEHSGNHSTHPVPSGKVLVLQ<br>SHWQTFHVSAVAAAAAAIFVIIIFYVRCCKK<br>KTSAAEGPELVSLQVLDQHPVGTSDHRDATQ<br>LGFQPLMSALGSTGSTEGA |

TABLE 2

| MICA epitopes recognized by human antibodies from patients responding to cancer immunotherapy (epitopes are underlined) | | |
|---|---|---|
| CM33322<br>Ab4 | SEQ ID<br>NO. 2 | LRR**TVPPMVNVTR**SEASEGNITVTCRAS<br>SFYPRNITLTWRQDGVSLSHDTQQWGDV<br>LPDGNGTYQTWVATRICQGEEQRFTCYM<br>EHSGNHSTHPVPS |
| CM33322<br>Ab28 | SEQ ID<br>NO. 3 | LRRTVPPMVNVTRSEASEGNITV**TCRAS**<br>**SFYPR**NITLTWRQDGVSLSHDTQQWGDV<br>LPDGNGTYQTWVATRICQGEEQRFTCYM<br>EHSGNHSTHPVPS |
| CM33322<br>Ab29 | SEQ ID<br>NO: 4 | LRRTVPPMVNVTRSEASEGNITVTCRAS<br>SFYPRNITLTWRQDGVSLSHDTQQW**GDV**<br>**LPDGNGTYQTWVATRIC**QGEEQRFTCYM<br>EHSGNHSTHPVPS |

TABLE 3

| MICA Epitopes with short flanking sequences | | |
|---|---|---|
| CM33322<br>Ab4 | SEQ ID<br>NO: 5 | YLESSVVLRR**TVPPMVNVTR**SEASEGNITV |
| CM33322<br>Ab4 | SEQ ID<br>NO: 6 | VVLRR**TVPPMVNVTR**SEASE |
| CM33322<br>Ab28 | SEQ ID<br>NO: 7 | SEASEGNITV**TCRASSFYPR**NITLTWRQDG |
| CM33322<br>Ab28 | SEQ ID<br>NO: 8 | GNITV**TCRASSFYPR**NITLT |
| CM33322<br>Ab29 | SEQ ID<br>NO: 9 | VSLSHDTQQW**GDVLPDGNGTYQTWVATRIC**<br>QGEEQRFTCY |
| CM33322<br>Ab29 | SEQ ID<br>NO: 10 | DTQQW**GDVLPDGNGTYQTWVATRIC**QGEEQ |

TABLE 4

| Minimal MICA epitopes | | |
|---|---|---|
| CM33322<br>Ab4 | SEQ ID<br>NO: 11 | TVPPMVNVTR |
| CM33322<br>Ab28 | SEQ ID<br>NO: 12 | TCRASSFYPR |
| CM33322<br>Ab29 | SEQ ID<br>NO: 13 | GDVLPDGNGTYQTWVATRIC |

TABLE 5

| MICB epitopes recognized by human antibodies from patients responding to cancer immunotherapy (epitopes are underlined) in MICB reference sequence (SEQ ID NO: 14) | | |
|---|---|---|
| CM33322<br>Ab4 | SEQ ID<br>NO: 14 | PHSLRYNLMVLSQDGSVQSGFLAEGHLDGQ<br>PFLRYDRQKRRAKPQGQWAEDVLGAKTWDT<br>ETEDLTENGQDLRRTLTHIKDQKGGLHSLQ<br>EIRVCEIHEDSSTRGSRHFYYDGELFLSQN<br>LETQESTVPQSSRAQTLAMNVTNFWKEDAM<br>KTKTHYRAMQADCLQKLQRYLKSGVAIRRT<br>VPPMVNVTCSEVSEGNITVTCRASSFYPRN<br>ITLTWRQDGVSLSHNTQQWGDVLPDGGTYQ<br>TWVATRIRQGEEQRFTCYMEHSGNHGTHPV<br>PSGKALVLQSQRTDFPYVSAAMPCFVIIII<br>LCVPCCKKKTSAAEGPELVSLQVLDQHPVG<br>TGDHRDAAQLGFQPLMSATGSTGSTEGA |
| CM33322<br>Ab28 | SEQ ID<br>NO: 14 | PHSLRYNLMVLSQDGSVQSGFLAEGHLDGQ<br>PFLRYDRQKRRAKPQGQWAEDVLGAKTWDT<br>ETEDLTENGQDLRRTLTHIKDQKGGLHSLQ<br>EIRVCEIHEDSSTRGSRHFYYDGELFLSQN<br>LETQESTVPQSSRAQTLAMNVTNFWKEDAM<br>KTKTHYRAMQADCLQKLQRYLKSGVAIRRT<br>VPPMVNVTCSEVSEGNITVTCRASSFYPRN<br>ITLTWRQDGVSLSHNTQQWGDVLPDGGTYQ<br>TWVATRIRQGEEQRFTCYMEHSGNHGTHPV<br>PSGKALVLQSQRTDFPYVSAAMPCFVIIII<br>LCVPCCKKKTSAAEGPELVSLQVLDQHPVG<br>TGDHRDAAQLGFQPLMSATGSTGSTEGA |
| CM33322<br>Ab29 | SEQ ID<br>NO: 14 | PHSLRYNLMVLSQDGSVQSGFLAEGHLDGQ<br>PFLRYDRQKRRAKPQGQWAEDVLGAKTWDT<br>ETEDLTENGQDLRRTLTHIKDQKGGLHSLQ<br>EIRVCEIHEDSSTRGSRHFYYDGELFLSQN<br>LETQESTVPQSSRAQTLAMNVTNFWKEDAM<br>KTKTHYRAMQADCLQKLQRYLKSGVAIRRT<br>VPPMVNVTCSEVSEGNITVTCRASSFYPRN<br>ITLTWRQDGVSLSHNTQQWGDVLPDGNGTY<br>QTWVATRIRQGEEQRFTCYMEHSGNHGTHP<br>VPSGKALVLQSQRTDFPYVSAAMPCFVIII<br>ILCVPCCKKKTSAAEGPELVSLQVLDQHPV<br>GTGDHRDAAQLGFQPLMSATGSTGSTEGA |

TABLE 6

| MICB Epitopes with short flanking sequences | | |
|---|---|---|
| CM33322<br>Ab4 | SEQ ID<br>NO: 15 | YLKSGVAIRR**TVPPMVNVTC**SEVSEGNITV |
| CM33322<br>Ab4 | SEQ ID<br>NO: 16 | VAIRR**TVPPMVNVTC**SEVSE |
| CM33322<br>Ab28 | SEQ ID<br>NO: 17 | SEVSEGNITV**TCRASSFYPR**NITLTWRQDG |
| CM33322<br>Ab28 | SEQ ID<br>NO: 18 | GNITV**TCRASSFYPR**NITLT |

TABLE 6-continued

| MICB Epitopes with short flanking sequences | | |
|---|---|---|
| CM33322 Ab29 | SEQ ID NO: 19 | VSLSHNTQQWGDVLPDGNGTYQTWVATRIR QGEEQRFTCY |
| CM33322 Ab29 | SEQ ID NO: 20 | NTQQWGDVLPDGNGTYQTWVATRIRQGEEQ |

TABLE 7

| Minimal MICB epitopes | | |
|---|---|---|
| CM33322 Ab4 | SEQ ID NO: 21 | TVPPMVNVTC |
| CM33322 Ab28 | SEQ ID NO: 22 | TCRASSFYPR |
| CM33322 Ab29 | SEQ ID NO: 23 | GDVLPDGNGTYQTWVATRIR |

The invention provides a vaccine composition suitable for administration to a human comprising, as an immunogenic component, at least one MIC peptide. In one embodiment, the at least one MIC peptide comprises or consists of the full-length alpha 3 domain of MICA or MICB, which domain corresponds to amino acids [181] *179* to 274 of the reference sequence, [(]SEQ ID NO: 1[)]. In another embodiment, the at least one peptide comprises or consists of a peptide epitope of a MIC peptide selected from the group consisting of any one of SEQ ID NOs: 2-13, or SEQ ID NOs: 15-23. In one embodiment, the at least one peptide consists of a peptide epitope selected from the group consisting of SEQ ID NOs: 11-13 or SEQ ID NOs: 21-23 and one or more flanking amino acids. In this context, the term "flanking amino acids" refers to the amino acids adjacent to the peptide epitope sequence in the full-length reference sequence [(]SEQ ID NO: 1 for MICA or SEQ ID NOs: 14 for MICB[)]. In certain embodiments, the at least one peptide epitope comprises 2, 4, 6, 8, or 10 flanking amino acids on either its N- or C-terminal end, or both. In one embodiment, the at least one peptide consists of a peptide epitope selected from the group consisting of SEQ ID NOs: 11-13 or SEQ ID NOs: 21-23 and one or more flanking amino acids such that the peptide consists of about 25 to 30 amino acids, or a length suitable for efficient induction of an antibody response to MIC proteins.

In one embodiment, the vaccine composition comprises, as its immunogenic component, at least two peptide epitopes of a MIC peptide selected from the group consisting of SEQ ID NOs: 2-13 or SEQ ID NOs: 15-23. In one embodiment, the vaccine composition comprises, as its immunogenic component, at least two peptide epitopes of a MIC peptide selected from the group consisting of SEQ ID NOs: 2-4 or SEQ ID NOs: 15-23. In one embodiment, the vaccine composition comprises, as its immunogenic component, at least two peptide epitopes of a MIC peptide selected from the group consisting of SEQ ID NOs: 5-10. In one embodiment, the vaccine composition comprises, as its immunogenic component, at least two peptide epitopes of a MIC peptide selected from the group consisting of SEQ ID NOs: 11-13 or SEQ ID NOs: 21-23.

In one embodiment, the vaccine composition comprises, as its immunogenic component, one or more peptide epitopes of a MIC peptide selected from the group consisting of SEQ ID NOs: 2-13 or SEQ ID NOs: 15-23 wherein the peptide epitopes are in the form of a linear sequence. In one embodiment, the peptide epitopes are in the form of a structurally constrained loop. In one embodiment, the peptides retain their native secondary structure, for example in the form of one or more loops. In one embodiment, the loop is created using either a disulfide bond or a chemical linker. Preferably, the loop is adapted to mimic the three-dimensional conformation of the MIC epitope on the human protein.

In another embodiment, the vaccine composition comprises a nucleic acid encoding one or more of the peptides of SEQ ID NOs: 2-13 or SEQ ID NOs: 15-23. The nucleic acid may be in the form of an expression vector, for example a plasmid or a viral vector, or the nucleic acid may be packaged into nanoparticles. In one embodiment, the nucleic acid is delivered to a subject by injection. In one embodiment, the nucleic acid is injected as purified DNA or in form of nanoparticles. In one embodiment, modified immune cells which have been modified to express the nucleic acid are injected. In one embodiment, the immune cells are modified via transfection or infection in vitro with a vector comprising the nucleic acid.

In one embodiment, the vaccine composition comprises, as its immunogenic component, a plurality of peptides, the plurality of peptides comprising or consisting of two or more peptides selected from the group consisting of SEQ ID NOs: 2-13 or SEQ ID NOs: 15-23. In one embodiment, the plurality of peptides comprises or consists of at least two peptides selected from the group consisting of SEQ ID NOs: 2-4 or SEQ ID NOs: 15-23. In one embodiment, the plurality of peptides comprises or consists of at least two selected from the group consisting of SEQ ID NOs: 5-10. In one embodiment, the plurality of peptides comprises or consists of at least two selected from the group consisting of SEQ ID NOs: 11-13 or SEQ ID NOs: 21-23.

In one embodiment, the at least one peptide or the plurality of peptides is conjugated to a second peptide containing an MHC-II epitope. Preferably, the amino acid sequence of the second peptide consists of 25 amino acids or less, or 15 amino acids or less. In specific embodiments, the second peptide consists of 9-12 amino acids, 10-18 amino acids, or 8-18 amino acids. Preferably, the second peptide contains a T cell epitope or a B cell epitope. In one embodiment, the T cell epitope is a T helper cell epitope effective to enhance B cell differentiation into antibody-producing plasma cells or a cytotoxic T cell epitope. In one embodiment, the epitopes are overlapping epitopes for different MHC alleles or epitopes presented by many MHC allotypes. In another embodiment, the epitopes are peptides presented by different MHC alleles.

The peptides which form or are incorporated into the vaccine compositions of the invention are preferably purified from contaminating chemical precursors, if chemically synthesized, or substantially free of cellular material from the cell or tissue source from which they are derived. In a specific embodiment, the peptides are 60%, preferably 65%, 70%, 75%, 80%, 85%, 90%, 95%, or 99% free of contaminating chemical precursors, proteins, lipids or nucleic acids. In a preferred embodiment, the peptides are substantially free of contaminating virus. Preferably, each composition for administering to a subject is at least 95%, at least 97%, or at least 99% free of contaminating virus.

In one embodiment, the at least one peptide or the plurality of peptides of a vaccine composition of the invention comprises or consists of one or more peptides that is at least 90%, at least 95%, at least 98%, or at least 99% identical to a peptide selected from the group consisting of any one of SEQ ID NOs: 2-13, SEQ ID NOs: 5-10, SEQ ID NOs: 11-13, SEQ ID NOs: 15-20, and SEQ ID NOs: 21-23.

In one embodiment, the at least one peptide or the plurality of peptides comprises or consists of one or more peptides that is at least 90%, at least 95%, at least 98%, or at least 99% similar to a peptide selected from the group consisting of any one of SEQ ID NOs: 2-13 or SEQ ID NOs: 15-23. In this context, the term "similar" refers to amino acid sequence similarity which is defined according to the number of conservative and non-conservative amino acid changes in a query sequence relative to a reference sequence. Conservative and non-conservative amino acid changes are known in the art. See, for example, W. R. Taylor, The Classification of Amino Acid Conservation, J. Theor. Biol. 1986 119:205-218, and D. Bordo and P. Argos, Suggestions for "Safe" Residue Substitutions in Site-Directed Mutagensis, 1991 J. Mol. Biol. 217:721-729. Generally, a conservative amino acid change refers to a substitution of one amino acid for another amino acid having substantially similar chemical properties, specifically with reference to the amino acid side chains. A non-conservative change refers to a substitution of one amino acid for another amino acid having substantially different chemical properties. Generally, conservative substitutions are those recognized in the art as being unlikely to affect the overall structure or biological function of the polypeptide, while non-conservative changes are recognized as more likely to affect structure and function.

Non-limiting examples of a conservative amino change include substitution of amino acids within the following groups: aliphatic, aromatic, polar, nonpolar, acidic, basic, phosphorylatable hydrophobic, hydrophilic, small nonpolar, small polar, large nonpolar, and large polar. Non-limiting examples of non-conservative amino acid changes include substitutions of amino acids between the foregoing groups.

In one embodiment, a conservative amino acid change is a substitution in which the substitution matrix for the pair of residues has a positive value. Examples of amino acid substitution matrices are known in the art, for example the BLOSUM50 matrix or the PAM250 matrix (see W. A. Pearson, Rapid and Sensitive Sequence Comparison with FASTP and FASTA, Meth. Enzymology, 1990 183:63-98, ed. R. Doolittle, Academic Press, San Diego). For further examples of scoring matrices and a comparison between them see M. S. Johnson and J. P. Overington, 1993, A Structural Basis for Sequence Comparisons: An Evaluation of Scoring Methodologies, J. Mol. Biol. 233:716-738.

In a preferred embodiment, a conservative amino acid change is a substitution of one amino acid for another amino acid within the same chemical group wherein the groups are selected from neutral and polar amino acids (Ser, Thr, Pro, Ala, Gly, Asn, Gln), negatively charged and polar amino acids (Asp, Glu), positively charged and polar amino acids (His, Arg, Lys), nonpolar amino acids lacking a ring structure (Met, Ile, Leu, Val), nonpolar amino acids having a ring structure (Phe, Tyr, Trp), and Cysteine.

In one embodiment, the vaccine composition of the invention comprises as its immunogenic component a chimeric protein which consists of two or more MIC peptide epitopes independently selected from the group consisting of SEQ ID NOs 2-13 or SEQ ID NOs: 15-23 in which the epitopes are linked. In one embodiment, the two or more MIC peptide epitopes are the same epitope. In another embodiment, the two or more MIC peptide epitopes comprise at least two MIC peptide epitopes that are different. In one embodiment, the vaccine composition comprises as its immunogenic component the chimeric protein displayed on the surface of a viral capsid, such as a Hepatitis B core capsid.

In one embodiment, the vaccine composition of the invention comprises as its immunogenic component a chimeric protein which consists of two or more MIC peptide epitopes selected from the group consisting of SEQ ID NOs 2-13 or SEQ ID NOs: 15-23 placed into an immunoglobulin (Ig) domain having a similar overall immunoglobulin fold compared to MICA. In one embodiment, the Ig domain is an Ig domain selected from one of the following: UL18 (human CMV), the C-terminal Ig domain of IFN-alpha/beta binding protein C12R (poxvirus decoy receptor, PDB ID:3OQ3), the N-terminal Ig domain of outer capsid protein from a T4-like bacteriophage (Hoc, PDB ID: 3SHS), and the human CMV protein US2 (PDB ID: 1IM3).

In one embodiment, the vaccine composition of the invention comprises two separate components adapted to be administered separately, the first component comprising an immunogen consisting of a first MIC peptide which comprises or consists of the full-length alpha 3 domain of MICA [SEQ ID NO: 1] or MICB; the second component comprising an immunogen consisting of one or more MIC peptide epitopes selected from the group consisting of SEQ ID NOs 2-13 or SEQ ID NOs: 15-23. In one embodiment, the vaccine composition comprises a first component comprising an immunogen consisting of a first MIC peptide which comprises or consists of the full-length alpha 3 domain of MICA [SEQ ID NO: 1]; and one or more additional components, each comprising an immunogen consisting of one or more MIC peptide epitopes selected from the group consisting of SEQ ID NOs 2-13 or SEQ ID NOs: 15-23. Preferably, the first component is administered before the second or additional components in a prime-boost fashion according to methods known in the art.

In one embodiment consistent with any of the foregoing embodiments, the vaccine composition of the invention may comprise one or more polynucleotide sequences encoding the MIC epitopes of SEQ ID NOs 1-23. In a further embodiment, the DNA encoding the one or more MIC epitopes is in the form of a nanoparticle comprising the DNA.

Peptide Variants

In some instances, amino acid sequences of the peptides disclosed herein can be modified and varied to create peptide variants (e.g., peptides with a defined sequence homology to the peptides disclosed herein), for example, so long as the antigen binding property of the peptide variant is maintained or improved relative to the unmodified peptide (antigen binding properties of any modified peptide can be assessed using the in vitro and/or in vivo assays described herein and/or techniques known in the art).

While peptide variants are generally observed and discussed at the amino acid level, the actual modifications are typically introduced or performed at the nucleic acid level. For example, variants with 80%, 85%, 90%, 95%, 96%, 97%, 98, or 99% amino acid sequence identity to the peptides of the invention can be generated by modifying the nucleic acids encoding the peptides or portions/fragments thereof, using techniques (e.g., cloning techniques) known in the art.

Amino acid sequence modifications typically fall into one or more of three classes: substitutional, insertional, or deletional modifications. Insertions include amino and/or terminal fusions as well as intra-sequence insertions of single or multiple amino acid residues. Insertions ordinarily will be smaller insertions than those of amino or carboxyl terminal fusions, for example, on the order of one to four residues.

Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions can be made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. In some instances, substitutions can be conservative amino acid substitutions. In some instances, peptides herein can include one or more conservative amino acid substitutions relative to a peptide of the invention. For example, variants can include 1, 2, 3, 4, 5, 6, 7, 8, 9, 10, 11, 12, 13, 14, 15, 16, 17, 18, 19, 20, 20-30, 30-40, or 40-50 conservative amino acid substitutions relative to a peptide shown in Table 1. Alternatively, variants can include 50 or fewer, 40 or fewer, 30 or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions relative to a peptide shown in Table 1. Such substitutions generally are made in accordance with the following [Table 2] *Table 8* and are referred to as conservative substitutions. Methods for predicting tolerance to protein modification are known in the art (see, e.g., Guo et al., Proc. Natl. Acad. Sci., USA, 101(25):9205-9210 (2004)).

TABLE 8

Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In some instances, substitutions are not conservative. For example, an amino acid in a peptide shown in Table 1 can be replaced with an amino acid that can alter some property or aspect of the peptide. In some instances, non-conservative amino acid substitutions can be made, e.g., to change the structure of a peptide, to change the binding properties of a peptide (e.g., to increase or decrease the affinity of binding of the peptide to an antigen and/or to alter increase or decrease the binding specificity of the peptide to the antigen).

In some instances, peptides and/or peptide variants can include or can be fragments of the peptides shown in Table 1. Such fragments can include, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42, 43, 44, 45, 46, 47, 48, 49, 50, 50-100, 101-150, fewer amino acids than the CDRs, FRs, and/or AAs shown in Table 1, e.g., so long as the fragments retain at least at portion of the binding properties of the full-length peptide (e.g., at least 50%, 60%, 70%, 80%, 90%, or 100% of the binding properties of the full-length peptide). Truncations can be made at the amino-terminus, the carboxy-terminus, and/or within the peptides herein.

In some instances, the interacting face of a peptide variant can be the same (e.g., substantially the same) as an unmodified peptide, e.g., to alter (e.g., increase or decrease), preserve, or maintain the binding properties of the peptide variant relative to the unmodified peptide. Methods for identifying the interacting face of a peptide are known in the art (Gong et al., BMC: Bioinformatics, 6:1471-2105 (2007); Andrade and Wei et al., Pure and Appl. Chem., 64(11):1777-1781 (1992); Choi et al., Proteins: Structure, Function, and Bioinformatics, 77(1):14-25 (2009); Park et al., BMC: and Bioinformatics, 10:1471-2105 (2009).

Those of skill in the art readily understand how to determine the identity of two polypeptides (e.g., an unmodified peptide and a peptide variant). For example, identity can be calculated after aligning the two sequences so that the identity is at its highest level. Another way of calculating identity can be performed by published algorithms. Optimal alignment of sequences for comparison may be conducted by the local identity algorithm of Smith and Waterman, Adv. Appl. Math, 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

In some instances, as described in more detail under the methods section below, therapeutic compositions disclosed herein can be produced using genetic material (e.g., DNA and/or mRNA) isolated and/or purified from immune cells (e.g., B cells, including memory B cells) obtained using the methods disclosed herein. Once such genetic material has been obtained, methods for using it to produce the therapeutic compositions disclosed herein are known in the art and/or are summarized below.

In some instances, peptides can include a detectable label. As used herein, a "label" refers to a moiety that has at least one element, isotope, or functional group incorporated into the moiety which enables detection of the peptide to which the label is attached. Labels can be directly attached (i.e., via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; labels that include immune or immunoreactive moieties, which may be antibodies or antigens, which may be bound to enzymes {e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101}mRh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99}mTc$, $^{14}C$, $^{13}N$, $^{15}0$, $^{32}P$, $^{33}P$, and $^{18}F$.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Peptides for use in the vaccine compositions of the invention can be made synthetically. In certain embodiments, one or more peptide bonds is replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefin bond (CH═CH); a fluoro substituted trans-olefin bond (CF═CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

In certain embodiments, the peptides are modified by one or more of acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation.

In one embodiment, the at least one peptide or the plurality of peptides is conjugated to a carrier protein. In one embodiment, the carrier protein is selected from tetanus toxin and diphtheria toxin. In another embodiment, the peptides are modified to extend in-vivo half-life by protecting against peptidase activity, for example as described in US 2009/0175821. In one embodiment, the peptides or modified peptides are further conjugated to polyethylene glycol (PEG), an alkyl group (e.g., C1-C20 straight or branched alkyl groups), a fatty acid radical, and combinations thereof.

In one embodiment, the plurality of peptides retain native secondary structure, for example, as short disulfide-linked loops. In another embodiment, secondary structure in the form of loops is created using disulfide bonds or by exposing the peptide to a chemical linker or cross-linker.

In one embodiment, the vaccine composition comprises a viral capsid protein engineered to display the at least one peptide or plurality of peptides on its surface. In one embodiment, the viral capsid protein is a hepatitis B capsid protein, for example as described in Proc Natl Acad Sci USA. 1999 Mar. 2; 96(5):1915-20.

In one embodiment, the at least one peptide or the plurality of peptides is contained within a micelle or nanoparticle structure. The use of micelles may be advantageous, for example, to retain peptide secondary structure as described in J. Am. Chem. Soc., 1998, 120 (39), pp 9979-9987.

Scaffold Embodiment

In one embodiment, the vaccine composition comprises or is in the form of a protein scaffold and the at least one peptide or the plurality of peptides is contained within the scaffold. A particularly preferred scaffold is a porous, polylactide-co-glycolide (PLG) polymer scaffold. In one embodiment, the scaffold further comprises one or both of a GM-CSF protein and a Toll-like receptor agonist. In one embodiment, the Toll-like receptor agonist comprises or consists of unmethylated CpG oligonucleotides (a TLR9 agonist). The scaffold may also contain autologous tumor cell lysates, where autologous is with reference to the subject being treated (i.e., lysates of the subject's own tumor cells). In one embodiment, the scaffold is the WDVAX scaffold described in US 2013/0202707, WO 2011/063336, and US 2012/0100182. The scaffold is also described in Nature Materials, published online 11 Jan. 2009 DOI: 10.1038/NMAT2357 and in Science Translation Medicine, Sci Transl Med 1, 8ra19 (2009); DOI: 10.1126/scitranslmed.3000359.

Additives and Adjuvants

The vaccine compositions of the invention may further comprise one or more pharmaceutically acceptable additives or adjuvants. In one embodiment, the vaccine composition does not comprise an adjuvant. In one embodiment, the one or more adjuvants is selected from the group consisting of an oil-based adjuvant, a CpG DNA adjuvant, a mineral salt adjuvant, a mineral salt gel adjuvant, a particulate adjuvant, a micro particulate adjuvant, a mucosal adjuvant, and a cytokine.

Adjuvants may comprise any number of delivery systems, for example, mineral salts, surface active agents, synthetic micro particles, oil-in-water emulsions, immunostimulatory complexes, liposomes, virosomes, and virus-like particles. Adjuvants further comprises one or more potentiators of the immune response such as microbial derivatives (e.g., bacterial products, toxins such as cholera toxin and heat labile toxin from E. coli, lipids, lipoproteins, nucleic acids, peptidogylcans, carbohydrates, peptides), cells, cytokines, (e.g., dendritic cells, IL-12, and GM-CSF), hormones, and small molecules. Adjuvants contemplated include, but are not limited to, oil-based adjuvants (e.g., Freund's adjuvant), CpG oligonucleotides (see Klinman 2003 Expert Rev. Vaccines 2:305-15) aluminum salt adjuvants, calcium salt adjuvants, emulsions and surfactant-based formulations (e.g., MF59, ASO2, montanide, ISA-51, ISA-720, and QA21). For a review of improvements in vaccine adjuvants, see Pashine et al. 2005, Nature Med. 11(4):S63-S68.

In one embodiment, the adjuvant comprises or consists of one or more toll-like receptor (TLR) agonists. In one embodiment, the TLR agonist is a pathogen associated agonist selected from the group consisting of triacylated lipopeptides (gram positive bacteria), Peptidoglycan (gram positive bacteria), bacterial lipoprotein, lipoteichoic acid, LPS (Porphyromonas gingivalis, Leptospira interrogans), GPI-anchor proteins (Trypanosoma cruzi), neisserial porins, hemagglutinin (MV), phospholipomannan (Candida), LAM (Mycobacteria), ssRNA virus (WNV), dsRNA virus (RSV, MCMV), LPS (Gram-negative bacteria), F-protein (RSV), mannan (Candida), glycoinositolphospholipids (Trypanosoma), envelope proteins (RSV and MMTV), flagellin (Flagellated bacteria), phenol-soluble modulin (Staphylococcus epidermidis), diacylated lipopeptides (Mycoplasma), LTA (Streptococcus), zymosan (Saccharomyces), viral ssRNA (Influenza, VSV, HIV, HCV), ssRNA from RNA virus, dsDNA viruses (HSV, MCMV), hemozoin (Plasmodium), and unmethylated CpG DNA (bacteria and viruses).

In one embodiment, the TLR agonist is a synthetic ligand selected from the group consisting of Pam3Cys, CFA, MALP2, Pam2Cys, FSL-1, Hib-OMPC, Poly I:C; poly A:U, AGP, MPL A, RC-529, MDF2I3, CFA, flagellin, MALP-2, Pam2Cys, FSL-1, Guanosine analogs, imidazoquinolines (e.g. Imiquimod, Aldara® R848, Esiquimod®), loxoribine, imidazoquinolines, Loxoribine, ssPolyU, 3M-012, and CpG-oligonucleotides.

Formulations

The vaccine compositions of the invention can be formulated using one or more physiologically acceptable carriers or excipients. For example, where a composition is formulated as a liquid, it may comprise sterile saline, a dextrose solution, or a buffered solution, or other pharmaceutically acceptable sterile fluid. In one embodiment, the formulations are for intradermal or subcutaneous administration. In one embodiment, the formulations are for inhalation or insufflation (either through the mouth or the nose). In one embodiment, the formulations are for oral, buccal, parenteral, vaginal, or rectal administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Preferably, the vaccine compositions are formulated to provide increased chemical stability of the peptide component during storage and transportation. For example, in one embodiment, the formulation prevents or reduces oligomerization of the peptides. In another example, the formulation prevents or reduces oxidation of the amino acid residues of the peptides. The formulations may be lyophilized or liquid formulations.

In one embodiment, the compositions are formulated for injection. In a preferred embodiment, the compositions are sterile lyophilized formulations, substantially free of contaminating cellular material, chemicals, virus, or toxins. In a particular embodiment, formulations for injection are provided in sterile single dosage containers. The formulations may or may not contain an added preservative. Liquid formulations may take such forms as suspensions, solutions or emulsions in oily or aqueous vehicles, and may contain formulatory agents such as suspending, stabilizing and/or dispersing agents.

In one embodiment, the formulation comprises liposomes.

In one embodiment, a vaccine composition of the invention is formulated with one or more other therapeutic agents used for the treatment of cancer.

The vaccine compositions of the invention are pharmaceutical compositions and can include one or more pharmaceutically acceptable carriers, additives, or vehicles. In one embodiment, the one or more pharmaceutically acceptable carriers, additives, or vehicles is selected from the group consisting of ion exchangers, alumina, aluminum stearate, lecithin, self-emulsifying drug delivery systems (SEDDS) such as d-I-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as I-, ϑ-, and K-cyclodextrin, may also be advantageously used to enhance delivery of compounds of the formulae described herein.

The vaccine compositions of the invention may also comprise a pharmaceutically acceptable acid, base or buffer to enhance the stability of the formulated compound or its delivery form.

In one embodiment, a vaccine composition of the invention is in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In one embodiment, a vaccine composition of the invention is in the form of an orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Methods of Treating and Administration

The vaccine compositions of the present invention are useful for the prophylaxis and treatment of cancer. Accordingly, the present invention provides methods of prophylaxis against cancer in a subject at risk of developing cancer and methods of treating cancer in a subject in need of such treatment. In one embodiment, the cancer is selected from the group consisting of prostate cancer, multiple myeloma, gliobastoma multiforme, and melanoma. In one embodiment, the cancer is melanoma.

In one embodiment, a vaccine composition of the invention is administered to a subject having a cancer associated with overexpression of MICA. In one embodiment, the cancer is selected from the group consisting of melanoma, lung, breast, kidney, ovarian, prostate, pancreatic, gastric, and colon carcinoma, lymphoma or leukemia. In one embodiment, the cancer is melanoma. In one embodiment, the cancer is a plasma cell malignancy, for example, multiple myeloma (MM) or pre-malignant condition of plasma cells. In some embodiments the subject has been diagnosed as having a cancer or as being predisposed to cancer.

The vaccine compositions of the invention may be administered separately or as part of a therapeutic regimen or combination therapy, as described below. The vaccine compositions of the invention may also be administered singly, or in multiple administrations, for example in a prime-boost strategy. In this context, the term "prime-boost" refers to the use of two different immunogens in succession. The two different immunogens are typically administered successively following a period of time such as 10 to 30 days or 10 to 60 days. In one embodiment, the period of time is from 2 to 4 weeks. Thus, for example, in one embodiment a vaccine composition of the invention is administered at time zero and a second vaccine composition of the invention (comprising a different immunogen) is administered following a period of time, for example from 10 to 30 days, from 10 to 60 days, or from 2 to 4 weeks.

In one embodiment, one or a plurality of different vaccine compositions of the invention is administered to the subject at multiple sites as described in U.S. Pat. No. 8,110,196. Preferably, each site drains to a lymph node or group of lymph nodes. In one embodiment, a vaccine composition of the invention is administered to multiple sites draining to two or more lymph nodes selected from the group consisting of the lymph nodes of the head and neck, the axillary lymph nodes, the tracheobronchial lymph nodes, the parietal lymph nodes, the gastric lymph nodes, the ileocolic lymph nodes, and the inguinal and subinguinal lymph nodes. In another embodiment, the sites are selected from the group consisting of the right arm, the left arm, the right thigh, the left thigh, the right shoulder, the left shoulder, the right breast, the left breast, the abdomen, the right buttock, and the left buttock. In one embodiment, the site is or drains to a nonencapsulated cluster of lymphoid tissue selected from the group consisting of the tonsils, the adenoids, the appendix, and Peyer's patches. In one embodiment, a vaccine composition of the invention is administered to a site that drains to the spleen.

In one embodiment, each vaccine composition is administered by a route independently selected from the group consisting of intradermally, subcutaneously, transdermally, intramuscularly, orally, rectally, vaginally, by inhalation, and a combination thereof. In one embodiment, at least one composition is injected directly into an anatomically distinct lymph node, lymph node cluster, or nonencapsulated cluster of lymphoid tissue.

Any suitable route of administration is encompassed by the methods of the invention, e.g. intradermal, subcutaneous, intravenous, intramuscular, or mucosal. Mucosal routes of administration include, but are not limited to, oral, rectal, vaginal, and nasal administration. In a preferred embodiment, at least one composition is administered transdermally, intradermally, subcutaneously, orally, rectally, vaginally or by inhalation. Any route approved by the Food and Drug Administration (FDA) can be used for the vaccine compositions of the invention. Exemplary methods of administration are described in the FDA's CDER Data Standards Manual, version number 004 (which is available at fda.give/cder/dsm/DRG/drg00301.htm).

Preferably, the route of administration is selected to target a composition to a particular site, for example, by injection directly into a lymph node or a lymph node cluster, by oral administration to target the lymph nodes of the stomach, by anal administration to target the lymph nodes of the rectum, by inhalation or aerosol to target the lymph nodes of the lungs, or by any other suitable route of administration.

Where the methods of the invention comprise administering a vaccine composition to multiple sites, each composition is preferably administered at substantially the same time, for example, within one to eight hours or during the same doctor's visit. In one embodiment, each composition is administered within one to two hours, within one to three hours, within one to four hours, or within one to five hours.

Where the vaccine composition is in the form of a scaffold, the method of vaccinating a subject comprises implanting the scaffold composition in the subject, preferably subcutaneous implantation. In certain embodiments, the method of vaccinating a subject may comprise implanting or injecting the scaffold vaccine composition in two or more areas of the subject's anatomy.

In one embodiment, the methods of the invention further comprise administering to the subject antigen presenting cells which have been sensitized with at least one MIC peptide selected from the group consisting of SEQ ID NOs: 2-13. In a preferred embodiment, the antigen presenting cells are dendritic cells.

In one embodiment, the method further comprises administering to the subject one or more adjuvants. In one embodiment, the one or more adjuvants is selected from the group consisting of an oil-based adjuvant, a CpG DNA adjuvant, a mineral salt adjuvant, a mineral salt gel adjuvant, a particulate adjuvant, a microparticulate adjuvant, a mucosal adjuvant, and a cytokine Such adjuvants may either be formulated with the compositions of the invention or administered separately from the compositions, e.g., prior to, concurrently with, or after the compositions are administered to the subject.

The methods disclosed herein can be applied to a wide range of species, e.g., humans, non-human primates (e.g., monkeys), horses, cattle, pigs, sheep, deer, elk, goats, dogs, cats, mustelids, rabbits, guinea pigs, hamsters, rats, and mice.

The terms "treat" or "treating," as used herein, refers to partially or completely alleviating, inhibiting, ameliorating, and/or relieving the disease or condition from which the subject is suffering. In some instances, treatment can result in the continued absence of the disease or condition from which the subject is suffering.

In general, methods include selecting a subject at risk for or with a condition or disease. In some instances, the subject's condition or disease can be treated with a pharmaceutical composition disclosed herein. For example, in some instances, methods include selecting a subject with cancer, e.g., wherein the subject's cancer can be treated by targeting one or both of MICA and/or angiopoetin-2.

In some instances, treatments methods can include a single administration, multiple administrations, and repeating administration as required for the prophylaxis or treatment of the disease or condition from which the subject is suffering. In some instances treatment methods can include assessing a level of disease in the subject prior to treatment, during treatment, and/or after treatment. In some instances, treatment can continue until a decrease in the level of disease in the subject is detected.

The terms "administer," "administering," or "administration," as used herein refers to implanting, absorbing, ingesting, injecting, or inhaling, the inventive peptide, regardless of form. In some instances, one or more of the peptides disclosed herein can be administered to a subject topically (e.g., nasally) and/or orally. For example, the methods herein include administration of an effective amount of compound or compound composition to achieve the desired or stated effect. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some instances, the disclosure provides methods for detecting immune cells e.g., B cells and/or memory B cells, from a human subject. Such methods can be used, for example, to monitor the levels of immune cells e.g., B cells and/or memory B cells, in a human subject, e.g., following an event. Exemplary events can include, but are not limited to, detection of diseases, infection; administration of a therapeutic composition disclosed herein, administration of a therapeutic agent or treatment regimen, administration of a vaccine, induction of an immune response. Such methods can be used clinically and/or for research.

Effective Amounts and Dosages

In one embodiment, an effective amount of a vaccine composition of the invention is the amount sufficient to reduce the severity of a cancer in a subject having cancer, or the amount sufficient to reduce or ameliorate the severity of one or more symptoms thereof, the amount sufficient to prevent the progression of the cancer, the amount sufficient to prevent further metastasis of the cancer, the amount sufficient to cause clinical regression of the cancer, or the amount sufficient to enhance or improve the therapeutic effect(s) of another therapy or therapeutic agent administered concurrently with, before, or after a vaccine composition of the invention.

Symptoms of cancer are well-known to those of skill in the art and include, without limitation, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

In one embodiment, the effective amount of a vaccine composition of the invention is the amount sufficient to produce an antibody secreting B cell or cytotoxic T cell mediated immune response directed against one or more of the peptides of the vaccine compositions of the invention. In one embodiment, the effective amount of a vaccine composition of the invention is the amount sufficient to produce an antibody secreting B cell or cytotoxic T cell mediated immune response directed against a cancer cell. The ability of the vaccine compositions of the invention to elicit an immune response can be determined using any routine method available to those of skill in the art. In one embodiment, the effective amount of each composition is the amount sufficient to produce a cytotoxic T cell response in the subject as measured, for example, by a mixed lymphocyte T cell assay.

In one embodiment, the effective amount of the vaccine composition administered to the subject, or at a particular site of the subject, is that amount which delivers 1 to 1000 micrograms of the one or more peptides of the composition. In one embodiment, the amount of peptides is 1 to 100 micrograms, 1 to 200 micrograms, 1 to 300 micrograms, 1 to 400 micrograms, 1 to 500 micrograms, 1 to 600 micrograms, 1 to 700 micrograms, 1 to 800 micrograms, or 1 to 900 micrograms. In another embodiment, the amount of peptides is 1 to 10 micrograms, 1 to 20 micrograms, 1 to 30 micrograms, 1 to 40 micrograms, 1 to 50 micrograms, 1 to 60 micrograms, 1 to 70 micrograms, 1 to 80 micrograms, or 1 to 90 micrograms. Preferably, the total amount of peptides administered to a subject does not exceed 5 milligrams, and most preferably the total amount does not exceed 2 milligrams.

Combination Therapy

The present invention also provides methods for the treatment or prophylaxis of cancer which comprise administering a vaccine composition of the invention to a subject in need thereof, along with one or more additional therapeutic agents or therapeutic regimens. In one embodiment, a vaccine composition of the invention is administered as part of a therapeutic regimen that includes surgery, a chemotherapeutic agent, or radiation therapy, an immunotherapy, or any combination of the foregoing.

In one embodiment, the therapeutic regimen comprises or further comprises a one or more immunostimulatory agents. In one embodiment, the one or more immunostimulatory agents is selected from the group consisting of an anti-CTLA-4 antibody or peptide, an anti-PD-1 antibody or peptide, an anti-PDL-1 antibody or peptide, an anti-OX40 (also known as CD134, TNFRSF4, ACT35 and/or TXGP1L) antibody or peptide, an anti-GITR (also known as TNFRSF18, AITR, and/or CD357) antibody or peptide, an anti-LAG-3 antibody or peptide, and/or an anti-TIM-3 antibody or peptide.

In one embodiment, the one or more immunostimulatory agents is selected from an anti-MICA antibody described in WO 2013/049517 or WO 2008/036981. In one embodiment, the one or more immunostimulatory agents is selected from CM33322 Ab4, CM33322 Ab28, and CM33322 Ab29, which are described in U.S. Provisional Application Nos. 61/792,034 and 61/913,198 and in U.S. application Ser. No. 14/025,573.

In one embodiment, the therapeutic regimen comprises or further comprises one or more cytokines. In one embodiment, the vaccine compositions of the invention comprise one or more cytokines. In one embodiment, at least one cytokine is an interleukin or an interferon. In one embodiment, at least one cytokine is an interleukin selected from the group consisting of IL-1.alpha., IL-1.beta., IL-2, IL-3, IL-4, IL-5, IL-6, IL-7, IL-8, IL-9, IL-11, IL-12, IL-13, IL-15, and IL-18. In another embodiment, at least one cytokine is an interferon selected from IFN.alpha., IFN-.beta., and IFN.gamma.

In one embodiment, a vaccine composition of the invention is administered as part of a therapeutic regimen that includes administering to the subject at least one chemotherapeutic agent selected from the group consisting of histone deacetylase inhibitors ("HDAC") inhibitors, proteasome inhibitors, alkylating agents, and topoisomerase inhibitors.

In one embodiment, the chemotherapeutic agent is an HDAC inhibitor selected from the group consisting of hydroxamic acid, Vorinostat (Zolinza), suberoylanilide hydroxamic acid (SAHA) (Merck), Trichostatin A (TSA), LAQ824 (Novartis), Panobinostat (LBH589) (Novartis), Belinostat (PXD101) (CuraGen), ITF2357 Italfarmaco SpA (Cinisello), Cyclic tetrapeptide, Depsipeptide (romidepsin, FK228) (Gloucester Pharmaceuticals), Benzamide, Entinostat (SNDX-275/MS-275) (Syndax Pharmaceuticals), MGCD0103 (Celgene), Short-chain aliphatic acids, Valproic acid, Phenyl butyrate, AN-9, pivanex (Titan Pharmaceutical), CHR-3996 (Chroma Therapeutics), and CHR-2845 (Chroma Therapeutics).

In one embodiment, the chemotherapeutic agent is a proteasome inhibitor selected from the group consisting of Bortezomib, (Millennium Pharmaceuticals), NPI-0052 (Nereus Pharmaceuticals), Carfilzomib (PR-171)(Onyx Pharmaceuticals), CEP 18770, and MLN9708.

In one embodiment, the chemotherapeutic agent is an alkylating agent such as mephalan.

In one embodiment, the chemotherapeutic agent is a topoisomerase inhibitor such as Adriamycin (doxorubicin).

In one embodiment, the therapeutic regimen comprises or further comprises one or more of chemotherapy, radiation therapy, cytokines, chemokines and other biologic signaling molecules, tumor specific vaccines, cellular cancer vaccines (e.g., GM-CSF transduced cancer cells), tumor specific monoclonal antibodies, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria) and gene therapy.

Kits

The invention provides a pharmaceutical pack or kit for carrying out the methods or therapeutic regimens of the invention. In one embodiment, the kit comprises a vaccine composition of the invention in lyophilized form. In one embodiment, the kit comprises a vaccine composition of the invention in the form of a protein scaffold.

In another embodiment, the kit further comprises in one or more additional containers a cytokine or an adjuvant.

The composition in each container may be in the form of a pharmaceutically acceptable solution, e.g., in combination with sterile saline, dextrose solution, or buffered solution, or other pharmaceutically acceptable sterile fluid. Alternatively, the composition may be lyophilized or desiccated; in this instance, the kit optionally further comprises in a separate container a pharmaceutically acceptable solution (e.g., saline, dextrose solution, etc.), preferably sterile, to reconstitute the composition to form a solution for injection purposes.

In another embodiment, the kit further comprises one or more reusable or disposable device(s) for administration (e.g, syringes, needles, dispensing pens), preferably packaged in sterile form, and/or a packaged alcohol pad. Instructions are optionally included for administration of the compositions by a clinician or by the patient. The kit may also comprise other materials, e.g., metal or plastic foil, such as a blister pack.

In some embodiments, the present disclosure provides methods for using any one or more of the vaccine compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, therapeutic compositions disclosed herein can be formulated for sale in the US, import into the US, and/or export from the US.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

EXAMPLES

The invention is further described in the following examples, which do not limit the scope of the invention described in the claims.

Example 1

Figure 3:
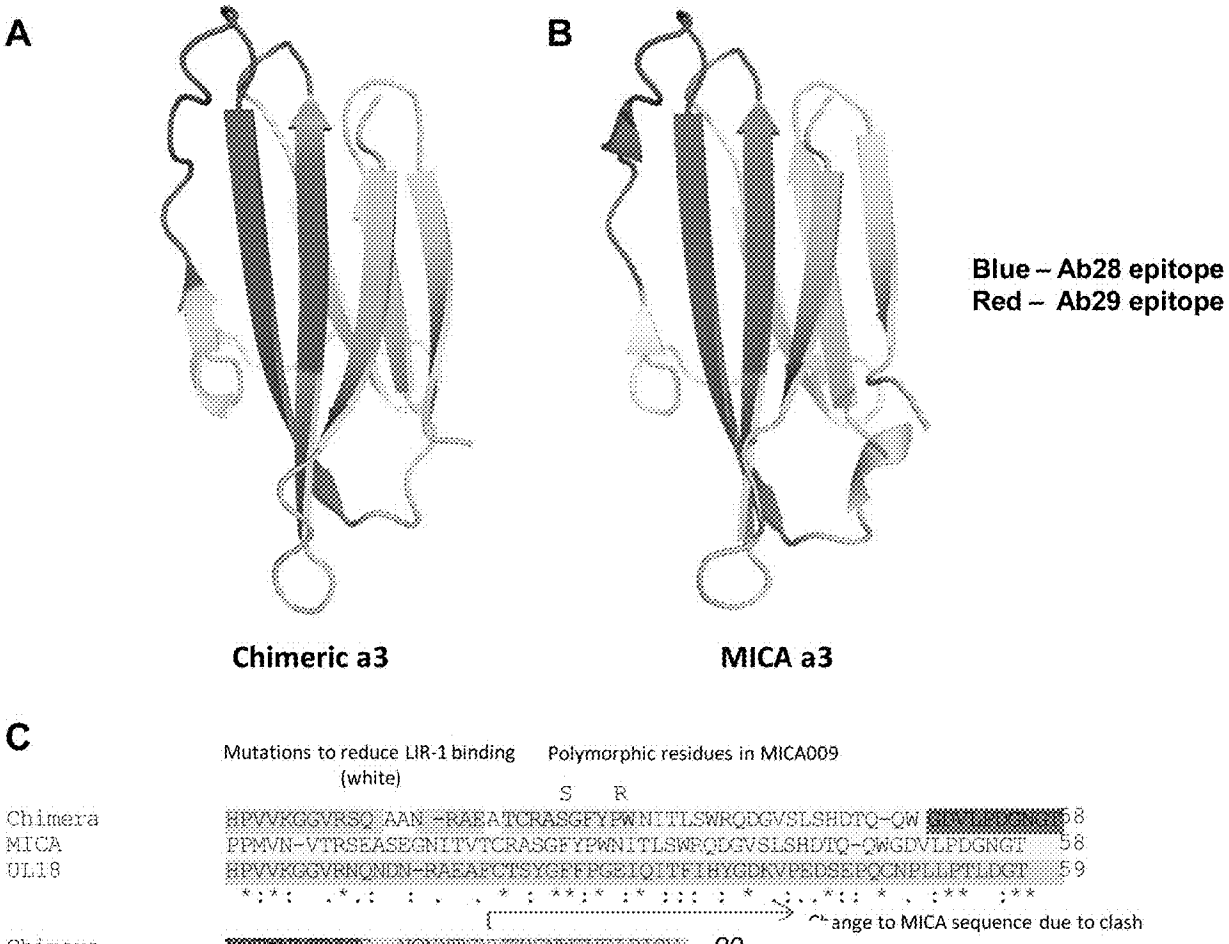
Figure 4:
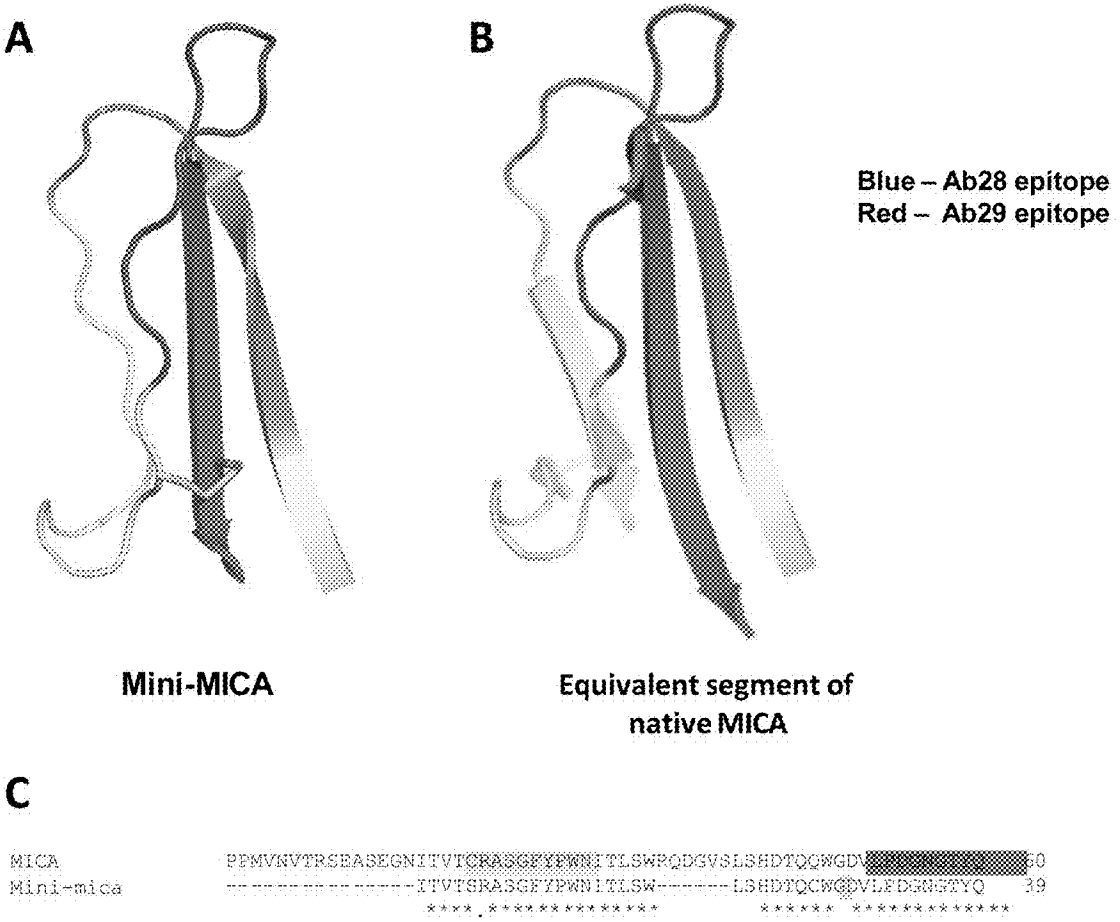

Design of Chimeric Protein with Properly Placed Epitopes for MICA Antibodies Two designs are shown in FIGS. 3 and 4. In the first design (FIG. 3) the two key epitopes recognized by human MICA antibodies were placed into an irrelevant protein (UL18 from human CMV) which has a similar overall immunoglobulin fold. This protein should be especially useful in the context of a booster following primary immunization with the human MICA α3 domain.

In the second design (FIG. 4) a minimal protein is created in which the two key epitopes are linked. This protein could be displayed on the surface of a viral capsid, such as Hepatitis B core capsid since N- and C-termini are in close vicinity.

Example 2

Therapeutic Activity of Human MICA Antibodies

Methods

The study design was approved by the institutional animal care and use committee (IACUC, protocol ID 08-049). Six-week-old male SCID (ICR-Prkdc$^{scid}$) mice were obtained from Taconic (Hudson, N.Y.). U937 cells were obtained from the American Type Culture Collection (ATCC, Manassas, Va.). For survival experiments, $2\times10^6$ cells were injected into the peritoneal cavity of naïve mice. Tumors were allowed to grow for ten days prior to randomization of mice into blinded treatment groups. Each treatment group contained ten mice, which is sufficient to discern survival benefits per the laboratory's previous experience. Randomization was based on in vivo imaging of mice, with treatment groups containing mice with similar overall mean signal intensity, indicating similar tumor burden. Treatments were blinded by an outside lab member not performing survival experiments. Investigators administered treatments in syringes labeled "Group A" or "Group B". Study was unblended at the conclusion of each survival experiment. Antibody treatments were given intravenously at a 100 μg/dose. Animals received three doses per week for a total of three weeks. Mice were bled weekly for the detection of circulating sMICA. All mice were included in the analysis. For short-term treatment, $2\times10^6$ U937 cells were implanted subcutaneously and allowed to establish tumors for ten days. Mice with palpable tumors were then treated for one 1 week (3×100 μg) with fully human antibodies (isotype, AML Ab2, Mel Ab28, or Mel Ab29). Eight days following initial treatment, mice were sacrificed, and tumors and spleens were excised, with tumor mass recorded. Tumors were cut into small pieces in Petri dishes containing 5 mL of digestion media containing RPMI media with 2% FBS, 50 U/ml collagenase type IV (Invitrogen), and 10 U/mL DNAse (Roche). Tissues were incubated in digestion medium at 37° C. for 2 hours. Tumors were then further dissociated using a gentle MACS Dissociator (Miltenyi Biotech). Supernatant of tumor cell suspension was saved for measurement of local sMICA concentrations. Cell suspensions were filtered through a 70 μM strainer and washed three times with PBS. Single cell suspensions were then stained for NK cell analysis with Zombie Yellow (viability dye, BioLegend), NKG2D-APC (CX5), Perforin-PE (eBioOMAK-D), CD45-PacBlue (30-F11), NKp46-PerCP/Cy5.5 (29A1.4), IFNγ-BV711 (XMG1.2), NK1.1-BV510 (PK136), CD16-APC/Cy7 (93), and CD49b-FITC (DX5). All antibodies were from BioLegend with the exception of Perforin (eBiosciences). An additional separate aliquot of cells was stained for MICA expression using anti-MICA-PE (clone 6D4, BioLegend).

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Human MICA/B Antibodies Potently Inhibit MICA Shedding in the Tumor Microenvironment A mouse model for assessment of the therapeutic efficacy of human MICA antibodies was established. Mice do not have MICA or MICB orthologs, but the mouse NKG2D receptor recognizes human MICA/B. See Liu et al. 2013, JCI 123(10): 4410-4422. We implanted human U937 cells, an AML cell line, in SCID mice that have NK cells but are deficient in T and B cells. This model allowed us to determine the impact of human MICA antibodies on NK cell mediated immunity against human tumor cells, but CD8 T cell responses could not be evaluated in this model. MICA antibody AML Ab2 was expressed with a murine IgG2a Fc segment to enable appropriate interaction with murine Fc receptors. The patient antibody had the human IgG1 isotype, which is functionally similar to mouse IgG2a. Mice were implanted with U937 cells and randomized to blinded treatment groups after ten days. Treatment for a three-week period (3×100 μg/week) provided a substantial survival benefit, with 55% survival at day 45 in the treatment group (AML Ab2) compared to 0% in the control group (Isotype). See FIG. 5A. Mechanistic studies demonstrated that sMICA became undetectable in sera after only two weeks of antibody treatment, while sMICA levels rose in the control group. See FIG. 5B.

We next examined the functional effects of treatment at an early time point using three fully human MICA/B antibodies. Following one week of treatment of SCID mice with subcutaneous tumors, sMICA levels were greatly reduced in mice in AML Ab2, Mel Ab28, and Mel Ab29 treatment groups compared to isotype control. See FIG. 5C. Flow cytometric analysis of tumors also revealed significantly increased expression of MICA on the surface of the tumor cells, mirroring in vitro results. See FIG. 5D. These results established that human MICA/B antibodies potently inhibit MICA shedding in the tumor microenvironment and thereby increase the density of MICA on tumor cells for recognition by cytotoxic lymphocytes.

Human MICA/B Antibodies Thus Improve Both Local and Systemic NK Cell Mediated Immunity Against Tumor Cells We performed further mechanistic studies on tumor-infiltrating NK cells at the one week time point of treatment. Inhibition of MICA shedding in tumors increased NKG2D surface expression on tumor-infiltrating NK cells. See FIG. 6A. Antibody treatment also resulted in >40-fold expansion of tumor-infiltrating NK cells and enhanced expression of the NKp46 receptor. See FIGS. 6B and 6C. Expanded tumor-infiltrating NK cells produced larger quantities of IFNγ, a cytokine critical for anti-tumor immunity, and expressed higher levels of perforin, a key molecule for cytotoxic function. See FIGS. 6d and 6e. To determine cytotoxic potential of NK cells in MICA/B antibody treated mice, we assessed killing of YAC-1 cells ex vivo by splenic NK cells. Enhanced killing was observed across all anti-MICA antibody treated mice relative to isotype treated mice. See FIG. 6F. Human MICA/B antibodies thus improve both local and systemic NK cell mediated immunity against tumor cells.

SEQUENCE LISTING

```
<160> NUMBER OF SEQ ID NOS: 45

<210> SEQ ID NO 1
<211> LENGTH: 360
<212> TYPE: PRT
<213> ORGANISM: Homo sapiens

<400> SEQUENCE: 1

His Ser Leu Arg Tyr Asn Leu Thr Val Leu Ser Trp Asp Gly Ser Val
1               5                   10                  15

Gln Ser Gly Phe Leu Ala Glu Val His Leu Asp Gly Gln Pro Phe Leu
            20                  25                  30

Arg Tyr Asp Arg Gln Lys Cys Arg Ala Lys Pro Gln Gly Gln Trp Ala
        35                  40                  45

Glu Asp Val Leu Gly Asn Lys Thr Trp Asp Arg Glu Thr Arg Asp Leu
    50                  55                  60

Thr Gly Asn Gly Lys Asp Leu Arg Met Thr Leu Ala His Ile Lys Asp
65                  70                  75                  80

Gln Lys Glu Gly Leu His Ser Leu Gln Glu Ile Arg Val Cys Glu Ile
                85                  90                  95

His Glu Asp Asn Ser Thr Arg Ser Ser Gln His Phe Tyr Tyr Asp Gly
            100                 105                 110

Glu Leu Phe Leu Ser Gln Asn Val Glu Thr Glu Glu Trp Thr Val Pro
        115                 120                 125

Gln Ser Ser Arg Ala Gln Thr Leu Ala Met Asn Val Arg Asn Phe Leu
    130                 135                 140

Lys Glu Asp Ala Met Lys Thr Lys Thr His Tyr His Ala Met His Ala
145                 150                 155                 160

Asp Cys Leu Gln Glu Leu Arg Arg Tyr Leu Glu Ser Ser Val Val Leu
                165                 170                 175

Arg Arg Thr Val Pro Pro Met Val Asn Val Thr Arg Ser Glu Ala Ser
            180                 185                 190

Glu Gly Asn Ile Thr Val Thr Cys Arg Ala Ser Ser Phe Tyr Pro Arg
        195                 200                 205

Asn Ile Thr Leu Thr Trp Arg Gln Asp Gly Val Ser Leu Ser His Asp
    210                 215                 220

Thr Gln Gln Trp Gly Asp Val Leu Pro Asp Gly Asn Gly Thr Tyr Gln
225                 230                 235                 240

Thr Trp Val Ala Thr Arg Ile Cys Gln Gly Glu Glu Gln Arg Phe Thr
                245                 250                 255

Cys Tyr Met Glu His Ser Gly Asn His Ser Thr His Pro Val Pro Ser
            260                 265                 270
```

```
Gly Lys Val Leu Val Leu Gln Ser His Trp Gln Thr Phe His Val Ser
        275                 280                 285

Ala Val Ala Ala Ala Ala Ala Ala Ile Phe Val Ile Ile Ile Phe Tyr
    290                 295                 300

Val Arg Cys Cys Lys Lys Lys Thr Ser Ala Ala Glu Gly Pro Glu Leu
305                 310                 315                 320

Val Ser Leu Gln Val Leu Asp Gln His Pro Val Gly Thr Ser Asp His
                325                 330                 335

Arg Asp Ala Thr Gln Leu Gly Phe Gln Pro Leu Met Ser Ala Leu Gly
            340                 345                 350

Ser Thr Gly Ser Thr Glu Gly Ala
        355                 360


<210> SEQ ID NO 2
<211> LENGTH: 97
<212> TYPE: PRT
<213> ORGANISM: Homo sapiens

<400> SEQUENCE: 2

Leu Arg Arg Thr Val Pro Pro Met Val Asn Val Thr Arg Ser Glu Ala
1               5                   10                  15

Ser Glu Gly Asn Ile Thr Val Thr Cys Arg Ala Ser Ser Phe Tyr Pro
            20                  25                  30

Arg Asn Ile Thr Leu Thr Trp Arg Gln Asp Gly Val Ser Leu Ser His
        35                  40                  45

Asp Thr Gln Gln Trp Gly Asp Val Leu Pro Asp Gly Asn Gly Thr Tyr
    50                  55                  60

Gln Thr Trp Val Ala Thr Arg Ile Cys Gln Gly Glu Glu Gln Arg Phe
65                  70                  75                  80

Thr Cys Tyr Met Glu His Ser Gly Asn His Ser Thr His Pro Val Pro
                85                  90                  95

Ser


<210> SEQ ID NO 3
<211> LENGTH: 97
<212> TYPE: PRT
<213> ORGANISM: Homo sapiens

<400> SEQUENCE: 3

Leu Arg Arg Thr Val Pro Pro Met Val Asn Val Thr Arg Ser Glu Ala
1               5                   10                  15

Ser Glu Gly Asn Ile Thr Val Thr Cys Arg Ala Ser Ser Phe Tyr Pro
            20                  25                  30

Arg Asn Ile Thr Leu Thr Trp Arg Gln Asp Gly Val Ser Leu Ser His
        35                  40                  45

Asp Thr Gln Gln Trp Gly Asp Val Leu Pro Asp Gly Asn Gly Thr Tyr
    50                  55                  60

Gln Thr Trp Val Ala Thr Arg Ile Cys Gln Gly Glu Glu Gln Arg Phe
65                  70                  75                  80

Thr Cys Tyr Met Glu His Ser Gly Asn His Ser Thr His Pro Val Pro
                85                  90                  95

Ser


<210> SEQ ID NO 4
<211> LENGTH: 97
<212> TYPE: PRT
<213> ORGANISM: Homo sapiens
```

<400> SEQUENCE: 4

Leu Arg Arg Thr Val Pro Pro Met Val Asn Val Thr Arg Ser Glu Ala
1 5 10 15

Ser Glu Gly Asn Ile Thr Val Thr Cys Arg Ala Ser Ser Phe Tyr Pro
20 25 30

Arg Asn Ile Thr Leu Thr Trp Arg Gln Asp Gly Val Ser Leu Ser His
35 40 45

Asp Thr Gln Gln Trp Gly Asp Val Leu Pro Asp Gly Asn Gly Thr Tyr
50 55 60

Gln Thr Trp Val Ala Thr Arg Ile Cys Gln Gly Glu Glu Gln Arg Phe
65 70 75 80

Thr Cys Tyr Met Glu His Ser Gly Asn His Ser Thr His Pro Val Pro
85 90 95

Ser

<210> SEQ ID NO 5
<211> LENGTH: 30
<212> TYPE: PRT
<213> ORGANISM: Homo sapiens

<400> SEQUENCE: 5

Tyr Leu Glu Ser Ser Val Val Leu Arg Arg Thr Val Pro Pro Met Val
1 5 10 15

Asn Val Thr Arg Ser Glu Ala Ser Glu Gly Asn Ile Thr Val
20 25 30

<210> SEQ ID NO 6
<211> LENGTH: 20
<212> TYPE: PRT
<213> ORGANISM: Homo sapiens

<400> SEQUENCE: 6

Val Val Leu Arg Arg Thr Val Pro Pro Met Val Asn Val Thr Arg Ser
1 5 10 15

Glu Ala Ser Glu
20

<210> SEQ ID NO 7
<211> LENGTH: 30
<212> TYPE: PRT
<213> ORGANISM: Homo sapiens

<400> SEQUENCE: 7

Ser Glu Ala Ser Glu Gly Asn Ile Thr Val Thr Cys Arg Ala Ser Ser
1 5 10 15

Phe Tyr Pro Arg Asn Ile Thr Leu Thr Trp Arg Gln Asp Gly
20 25 30

<210> SEQ ID NO 8
<211> LENGTH: 20
<212> TYPE: PRT
<213> ORGANISM: Homo sapiens

<400> SEQUENCE: 8

Gly Asn Ile Thr Val Thr Cys Arg Ala Ser Ser Phe Tyr Pro Arg Asn
1 5 10 15

Ile Thr Leu Thr
20

<210> SEQ ID NO 9
<211> LENGTH: 40
<212> TYPE: PRT
<213> ORGANISM: Homo sapiens

<400> SEQUENCE: 9

Val Ser Leu Ser His Asp Thr Gln Gln Trp Gly Asp Val Leu Pro Asp
1 5 10 15

Gly Asn Gly Thr Tyr Gln Thr Trp Val Ala Thr Arg Ile Cys Gln Gly
20 25 30

Glu Glu Gln Arg Phe Thr Cys Tyr
35 40

<210> SEQ ID NO 10
<211> LENGTH: 30
<212> TYPE: PRT
<213> ORGANISM: Homo sapiens

<400> SEQUENCE: 10

Asp Thr Gln Gln Trp Gly Asp Val Leu Pro Asp Gly Asn Gly Thr Tyr
1 5 10 15

Gln Thr Trp Val Ala Thr Arg Ile Cys Gln Gly Glu Glu Gln
20 25 30

<210> SEQ ID NO 11
<211> LENGTH: 10
<212> TYPE: PRT
<213> ORGANISM: Homo sapiens

<400> SEQUENCE: 11

Thr Val Pro Pro Met Val Asn Val Thr Arg
1 5 10

<210> SEQ ID NO 12
<211> LENGTH: 10
<212> TYPE: PRT
<213> ORGANISM: Homo sapiens

<400> SEQUENCE: 12

Thr Cys Arg Ala Ser Ser Phe Tyr Pro Arg
1 5 10

<210> SEQ ID NO 13
<211> LENGTH: 20
<212> TYPE: PRT
<213> ORGANISM: Homo sapiens

<400> SEQUENCE: 13

Gly Asp Val Leu Pro Asp Gly Asn Gly Thr Tyr Gln Thr Trp Val Ala
1 5 10 15

Thr Arg Ile Cys
20

<210> SEQ ID NO 14
<211> LENGTH: 358
<212> TYPE: PRT
<213> ORGANISM: Homo sapiens

<400> SEQUENCE: 14

Pro His Ser Leu Arg Tyr Asn Leu Met Val Leu Ser Gln Asp Gly Ser
1 5 10 15

Val Gln Ser Gly Phe Leu Ala Glu Gly His Leu Asp Gly Gln Pro Phe

```
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Lys Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
    210                 215                 220

Asn Thr Gln Gln Trp Gly Asp Val Leu Pro Asp Gly Gly Thr Tyr Gln
225                 230                 235                 240

Thr Trp Val Ala Thr Arg Ile Arg Gln Gly Glu Glu Gln Arg Phe Thr
                245                 250                 255

Cys Tyr Met Glu His Ser Gly Asn His Gly Thr His Pro Val Pro Ser
            260                 265                 270

Gly Lys Ala Leu Val Leu Gln Ser Gln Arg Thr Asp Phe Pro Tyr Val
        275                 280                 285

Ser Ala Ala Met Pro Cys Phe Val Ile Ile Ile Ile Leu Cys Val Pro
    290                 295                 300

Cys Cys Lys Lys Lys Thr Ser Ala Ala Glu Gly Pro Glu Leu Val Ser
305                 310                 315                 320

Leu Gln Val Leu Asp Gln His Pro Val Gly Thr Gly Asp His Arg Asp
                325                 330                 335

Ala Ala Gln Leu Gly Phe Gln Pro Leu Met Ser Ala Thr Gly Ser Thr
            340                 345                 350

Gly Ser Thr Glu Gly Ala
        355


<210> SEQ ID NO 15
<211> LENGTH: 30
<212> TYPE: PRT
<213> ORGANISM: Homo sapiens

<400> SEQUENCE: 15

Tyr Leu Lys Ser Gly Val Ala Ile Arg Arg Thr Val Pro Pro Met Val
1               5                   10                  15

Asn Val Thr Cys Ser Glu Val Ser Glu Gly Asn Ile Thr Val
            20                  25                  30
```

<210> SEQ ID NO 16
<211> LENGTH: 20
<212> TYPE: PRT
<213> ORGANISM: Homo sapiens

<400> SEQUENCE: 16

Val Ala Ile Arg Arg Thr Val Pro Pro Met Val Asn Val Thr Cys Ser
1 5 10 15

Glu Val Ser Glu
20

<210> SEQ ID NO 17
<211> LENGTH: 30
<212> TYPE: PRT
<213> ORGANISM: Homo sapiens

<400> SEQUENCE: 17

Ser Glu Val Ser Glu Gly Asn Ile Thr Val Thr Cys Arg Ala Ser Ser
1 5 10 15

Phe Tyr Pro Arg Asn Ile Thr Leu Thr Trp Arg Gln Asp Gly
20 25 30

<210> SEQ ID NO 18
<211> LENGTH: 20
<212> TYPE: PRT
<213> ORGANISM: Homo sapiens

<400> SEQUENCE: 18

Gly Asn Ile Thr Val Thr Cys Arg Ala Ser Ser Phe Tyr Pro Arg Asn
1 5 10 15

Ile Thr Leu Thr
20

<210> SEQ ID NO 19
<211> LENGTH: 40
<212> TYPE: PRT
<213> ORGANISM: Homo sapiens

<400> SEQUENCE: 19

Val Ser Leu Ser His Asn Thr Gln Gln Trp Gly Asp Val Leu Pro Asp
1 5 10 15

Gly Asn Gly Thr Tyr Gln Thr Trp Val Ala Thr Arg Ile Arg Gln Gly
20 25 30

Glu Glu Gln Arg Phe Thr Cys Tyr
35 40

<210> SEQ ID NO 20
<211> LENGTH: 30
<212> TYPE: PRT
<213> ORGANISM: Homo sapiens

<400> SEQUENCE: 20

Asn Thr Gln Gln Trp Gly Asp Val Leu Pro Asp Gly Asn Gly Thr Tyr
1 5 10 15

Gln Thr Trp Val Ala Thr Arg Ile Arg Gln Gly Glu Glu Gln
20 25 30

<210> SEQ ID NO 21
<211> LENGTH: 10
<212> TYPE: PRT
<213> ORGANISM: Homo sapiens

<400> SEQUENCE: 21

Thr Val Pro Pro Met Val Asn Val Thr Cys
1 5 10

<210> SEQ ID NO 22
<211> LENGTH: 10
<212> TYPE: PRT
<213> ORGANISM: Homo sapiens

<400> SEQUENCE: 22

Thr Cys Arg Ala Ser Ser Phe Tyr Pro Arg
1 5 10

<210> SEQ ID NO 23
<211> LENGTH: 20
<212> TYPE: PRT
<213> ORGANISM: Homo sapiens

<400> SEQUENCE: 23

Gly Asp Val Leu Pro Asp Gly Asn Gly Thr Tyr Gln Thr Trp Val Ala
1 5 10 15

Thr Arg Ile Arg
20

<210> SEQ ID NO 24
<211> LENGTH: 114
<212> TYPE: PRT
<213> ORGANISM: Homo sapiens

<400> SEQUENCE: 24

His Ala Asp Cys Leu Gln Glu Leu Arg Arg Tyr Leu Glu Ser Ser Val
1 5 10 15

Val Leu Arg Arg Thr Val Pro Pro Met Val Asn Val Thr Arg Ser Glu
20 25 30

Ala Ser Glu Gly Asn Ile Thr Val Thr Cys Arg Ala Ser Ser Phe Tyr
35 40 45

Pro Arg Asn Ile Thr Leu Thr Trp Arg Gln Asp Gly Val Ser Leu Ser
50 55 60

His Asp Thr Gln Gln Trp Gly Asp Val Leu Pro Asp Gly Asn Gly Thr
65 70 75 80

Tyr Gln Thr Trp Val Ala Thr Arg Ile Cys Gln Gly Glu Glu Gln Arg
85 90 95

Phe Thr Cys Tyr Met Glu His Ser Gly Asn His Ser Thr His Pro Val
100 105 110

Pro Ser

<210> SEQ ID NO 25
<211> LENGTH: 114
<212> TYPE: PRT
<213> ORGANISM: Homo sapiens

<400> SEQUENCE: 25

His Ala Asp Cys Leu Gln Glu Leu Arg Arg Tyr Leu Lys Ser Gly Val
1 5 10 15

Val Leu Arg Arg Thr Val Pro Pro Met Val Asn Val Thr Arg Ser Glu
20 25 30

Ala Ser Glu Gly Asn Ile Thr Val Thr Cys Arg Ala Ser Gly Phe Tyr
35 40 45

Pro Trp Asn Ile Thr Leu Ser Trp Arg Gln Asp Gly Val Ser Leu Ser

```
    50                  55                  60

His Asp Thr Gln Gln Trp Gly Asp Val Leu Pro Asp Gly Asn Gly Thr
65                  70                  75                  80

Tyr Gln Thr Trp Val Ala Thr Arg Ile Cys Gln Gly Glu Glu Gln Arg
                85                  90                  95

Phe Thr Cys Tyr Met Glu His Ser Gly Asn His Ser Thr His Pro Val
            100                 105                 110

Pro Ser


<210> SEQ ID NO 26
<211> LENGTH: 114
<212> TYPE: PRT
<213> ORGANISM: Homo sapiens

<400> SEQUENCE: 26

His Ala Asp Cys Leu Gln Glu Leu Arg Arg Tyr Leu Glu Ser Ser Val
1               5                   10                  15

Val Leu Arg Arg Arg Val Pro Pro Met Val Asn Val Thr Arg Ser Glu
            20                  25                  30

Ala Ser Glu Gly Asn Ile Thr Val Thr Cys Arg Ala Ser Ser Phe Tyr
        35                  40                  45

Pro Arg Asn Ile Thr Leu Thr Trp Arg Gln Asp Gly Val Ser Leu Ser
    50                  55                  60

His Asp Thr Gln Gln Trp Gly Asp Val Leu Pro Asp Gly Asn Gly Thr
65                  70                  75                  80

Tyr Gln Thr Trp Val Ala Thr Arg Ile Cys Gln Gly Glu Glu Gln Arg
                85                  90                  95

Phe Thr Cys Tyr Met Glu His Ser Gly Asn His Ser Thr His Pro Val
            100                 105                 110

Pro Ser


<210> SEQ ID NO 27
<211> LENGTH: 114
<212> TYPE: PRT
<213> ORGANISM: Homo sapiens

<400> SEQUENCE: 27

His Ala Asp Cys Leu Gln Glu Leu Arg Arg Tyr Leu Lys Ser Gly Val
1               5                   10                  15

Val Leu Arg Arg Thr Val Pro Pro Met Val Asn Val Thr Arg Ser Glu
            20                  25                  30

Ala Ser Glu Gly Asn Ile Thr Val Thr Cys Arg Ala Ser Gly Phe Tyr
        35                  40                  45

Pro Trp Asn Ile Thr Leu Ser Trp Arg Gln Asp Gly Val Ser Leu Ser
    50                  55                  60

His Asp Thr Gln Gln Trp Gly Asp Val Leu Pro Asp Gly Asn Gly Thr
65                  70                  75                  80

Tyr Gln Thr Trp Val Ala Thr Arg Ile Cys Gln Gly Glu Glu Gln Arg
                85                  90                  95

Phe Thr Cys Tyr Met Glu His Ser Gly Asn His Ser Thr His Pro Val
            100                 105                 110

Pro Ser


<210> SEQ ID NO 28
<211> LENGTH: 114
<212> TYPE: PRT
```

<213> ORGANISM: Homo sapiens

<400> SEQUENCE: 28

His Ala Asp Cys Leu Gln Glu Leu Arg Arg Tyr Leu Lys Ser Gly Val
1 5 10 15

Val Leu Arg Arg Thr Val Pro Pro Met Val Asn Val Thr Arg Ser Glu
20 25 30

Ala Ser Glu Gly Asn Ile Thr Val Thr Cys Arg Ala Ser Gly Phe Tyr
35 40 45

Pro Trp Asn Ile Thr Leu Ser Trp Arg Gln Asp Gly Val Ser Leu Ser
50 55 60

His Asp Thr Gln Gln Trp Gly Asp Val Leu Pro Asp Gly Asn Gly Thr
65 70 75 80

Tyr Gln Thr Trp Val Ala Thr Arg Ile Cys Gln Gly Glu Glu Gln Arg
85 90 95

Phe Thr Cys Tyr Met Glu His Ser Gly Asn His Ser Thr His Pro Val
100 105 110

Pro Ser

<210> SEQ ID NO 29
<211> LENGTH: 114
<212> TYPE: PRT
<213> ORGANISM: Homo sapiens

<400> SEQUENCE: 29

His Ala Asp Cys Leu Gln Glu Leu Arg Arg Tyr Leu Lys Ser Gly Val
1 5 10 15

Val Leu Arg Arg Thr Val Pro Pro Met Val Asn Val Thr Arg Ser Glu
20 25 30

Ala Ser Glu Gly Asn Ile Thr Val Thr Cys Arg Ala Ser Gly Phe Tyr
35 40 45

Pro Trp Asn Ile Thr Leu Ser Trp Arg Gln Asp Gly Val Ser Leu Ser
50 55 60

His Asp Thr Gln Gln Trp Gly Asp Val Leu Pro Asp Gly Asn Gly Thr
65 70 75 80

Tyr Gln Thr Trp Val Ala Thr Arg Ile Cys Gln Gly Glu Glu Gln Arg
85 90 95

Phe Thr Cys Tyr Met Glu His Ser Gly Asn His Ser Thr His Pro Val
100 105 110

Pro Ser

<210> SEQ ID NO 30
<211> LENGTH: 114
<212> TYPE: PRT
<213> ORGANISM: Homo sapiens

<400> SEQUENCE: 30

His Ala Asp Cys Leu Gln Glu Leu Arg Arg Tyr Leu Glu Ser Ser Val
1 5 10 15

Val Leu Arg Arg Thr Val Pro Pro Met Val Asn Val Thr Arg Ser Glu
20 25 30

Ala Ser Glu Gly Asn Ile Thr Val Thr Cys Arg Ala Ser Ser Phe Tyr
35 40 45

Pro Arg Asn Ile Ile Leu Thr Trp Arg Gln Asp Gly Val Ser Leu Ser
50 55 60

His Asp Thr Gln Gln Trp Gly Asp Val Leu Pro Asp Gly Asn Gly Thr

```
65                  70                  75                  80

Tyr Gln Thr Trp Val Ala Thr Arg Ile Cys Arg Gly Glu Glu Gln Arg
                85                  90                  95

Phe Thr Cys Tyr Met Glu His Ser Gly Asn His Ser Thr His Pro Val
            100                 105                 110

Pro Ser


<210> SEQ ID NO 31
<211> LENGTH: 114
<212> TYPE: PRT
<213> ORGANISM: Homo sapiens

<400> SEQUENCE: 31

His Ala Asp Cys Leu Gln Glu Leu Arg Arg Tyr Leu Lys Ser Gly Val
1               5                   10                  15

Val Leu Arg Arg Thr Val Pro Pro Met Val Asn Val Thr Arg Ser Glu
            20                  25                  30

Ala Ser Glu Gly Asn Ile Thr Val Thr Cys Arg Ala Ser Gly Phe Tyr
        35                  40                  45

Pro Trp Asn Ile Thr Leu Ser Trp Arg Gln Asp Gly Val Ser Leu Ser
    50                  55                  60

His Asp Thr Gln Gln Trp Gly Asp Val Leu Pro Asp Gly Asn Gly Thr
65                  70                  75                  80

Tyr Gln Thr Trp Val Ala Thr Arg Ile Cys Gln Gly Glu Glu Gln Arg
                85                  90                  95

Phe Thr Cys Tyr Met Glu His Ser Gly Asn His Ser Thr His Pro Val
            100                 105                 110

Pro Ser


<210> SEQ ID NO 32
<211> LENGTH: 114
<212> TYPE: PRT
<213> ORGANISM: Homo sapiens

<400> SEQUENCE: 32

His Ala Asp Cys Leu Gln Glu Leu Arg Arg Tyr Leu Lys Ser Gly Val
1               5                   10                  15

Val Leu Arg Arg Thr Val Pro Pro Met Val Asn Val Thr Arg Ser Glu
            20                  25                  30

Ala Ser Glu Gly Asn Ile Thr Val Thr Cys Arg Ala Ser Gly Phe Tyr
        35                  40                  45

Pro Trp Asn Ile Thr Leu Ser Trp Arg Gln Asp Gly Val Ser Leu Ser
    50                  55                  60

His Asp Thr Gln Gln Trp Gly Asp Val Leu Pro Asp Gly Asn Gly Thr
65                  70                  75                  80

Tyr Gln Thr Trp Val Ala Thr Arg Ile Cys Gln Gly Glu Glu Gln Arg
                85                  90                  95

Phe Thr Cys Tyr Met Glu His Ser Gly Asn His Ser Thr His Pro Val
            100                 105                 110

Pro Ser


<210> SEQ ID NO 33
<211> LENGTH: 114
<212> TYPE: PRT
<213> ORGANISM: Homo sapiens

<400> SEQUENCE: 33
```

His Ala Asp Cys Leu Gln Glu Leu Arg Arg Tyr Leu Lys Ser Gly Val
1 5 10 15

Val Leu Arg Arg Thr Val Pro Pro Met Val Asn Val Thr Arg Ser Glu
20 25 30

Ala Ser Glu Gly Asn Ile Thr Val Thr Cys Arg Ala Ser Gly Phe Tyr
35 40 45

Pro Trp Asn Ile Thr Leu Ser Trp Arg Gln Asp Gly Val Ser Leu Ser
50 55 60

His Asp Thr Gln Gln Trp Gly Asp Val Leu Pro Asp Gly Asn Gly Thr
65 70 75 80

Tyr Gln Thr Trp Val Ala Thr Arg Ile Cys Gln Gly Glu Glu Gln Arg
85 90 95

Phe Thr Cys Tyr Met Glu His Ser Gly Asn His Ser Thr His Pro Val
100 105 110

Pro Ser

<210> SEQ ID NO 34
<211> LENGTH: 114
<212> TYPE: PRT
<213> ORGANISM: Homo sapiens

<400> SEQUENCE: 34

His Ala Asp Cys Leu Gln Glu Leu Arg Arg Tyr Leu Glu Ser Gly Val
1 5 10 15

Val Leu Arg Arg Thr Val Pro Pro Met Val Asn Val Thr Arg Ser Glu
20 25 30

Ala Ser Glu Gly Asn Ile Thr Val Thr Cys Arg Ala Ser Ser Phe Tyr
35 40 45

Pro Arg Asn Ile Ile Leu Thr Trp Arg Gln Asp Gly Val Ser Leu Ser
50 55 60

His Asp Thr Gln Gln Trp Gly Asp Val Leu Pro Asp Gly Asn Gly Thr
65 70 75 80

Tyr Gln Thr Trp Val Ala Thr Arg Ile Cys Arg Gly Glu Glu Gln Arg
85 90 95

Phe Thr Cys Tyr Met Glu His Ser Gly Asn His Ser Thr His Pro Val
100 105 110

Pro Ser

<210> SEQ ID NO 35
<211> LENGTH: 100
<212> TYPE: PRT
<213> ORGANISM: Homo sapiens

<400> SEQUENCE: 35

Tyr Leu Lys Ser Gly Val Ala Ile Arg Arg Thr Val Pro Pro Met Val
1 5 10 15

Asn Val Thr Cys Ser Glu Val Ser Glu Gly Asn Ile Thr Val Thr Cys
20 25 30

Arg Ala Ser Ser Phe Tyr Pro Arg Asn Ile Thr Leu Thr Trp Arg Gln
35 40 45

Asp Gly Val Ser Leu Ser His Asn Thr Gln Gln Trp Gly Asp Val Leu
50 55 60

Pro Asp Gly Asn Gly Thr Tyr Gln Thr Trp Val Ala Thr Arg Ile Arg
65 70 75 80

Gln Gly Glu Glu Gln Arg Phe Thr Cys Tyr Met Glu His Ser Gly Asn

```
                85                  90                  95

His Gly Thr His
            100


<210> SEQ ID NO 36
<211> LENGTH: 100
<212> TYPE: PRT
<213> ORGANISM: Homo sapiens

<400> SEQUENCE: 36

Tyr Leu Lys Ser Gly Val Ala Ile Arg Arg Thr Val Pro Pro Met Val
1               5                   10                  15

Asn Val Ile Cys Ser Glu Val Ser Glu Gly Asn Ile Thr Val Thr Cys
            20                  25                  30

Arg Ala Ser Ser Phe Tyr Pro Arg Asn Ile Thr Leu Thr Trp Arg Gln
        35                  40                  45

Asp Gly Val Ser Leu Ser His Asn Thr Gln Gln Trp Gly Asp Val Leu
    50                  55                  60

Pro Asp Gly Asn Gly Thr Tyr Gln Thr Trp Val Ala Thr Arg Ile Arg
65                  70                  75                  80

Gln Gly Glu Glu Gln Arg Phe Thr Cys Tyr Met Glu His Ser Gly Asn
                85                  90                  95

His Gly Thr His
            100


<210> SEQ ID NO 37
<211> LENGTH: 100
<212> TYPE: PRT
<213> ORGANISM: Homo sapiens

<400> SEQUENCE: 37

Tyr Leu Lys Ser Gly Val Ala Ile Arg Arg Thr Val Pro Pro Met Val
1               5                   10                  15

Asn Val Thr Cys Ser Glu Lys Ser Glu Gly Asn Ile Thr Val Thr Cys
            20                  25                  30

Arg Ala Ser Ser Phe Tyr Pro Arg Asn Ile Thr Leu Thr Trp Arg Gln
        35                  40                  45

Asp Gly Val Ser Leu Ser His Asn Thr Gln Gln Trp Gly Asp Val Leu
    50                  55                  60

Pro Asp Gly Asn Gly Thr Tyr Gln Thr Trp Val Ala Thr Arg Ile Arg
65                  70                  75                  80

Gln Gly Glu Glu Gln Arg Phe Thr Cys Tyr Met Glu His Ser Gly Asn
                85                  90                  95

His Gly Thr His
            100


<210> SEQ ID NO 38
<211> LENGTH: 100
<212> TYPE: PRT
<213> ORGANISM: Homo sapiens

<400> SEQUENCE: 38

Tyr Leu Lys Ser Gly Val Ala Ile Arg Arg Thr Val Pro Pro Met Val
1               5                   10                  15

Asn Val Thr Cys Ser Glu Val Ser Glu Gly Asn Ile Thr Val Thr Cys
            20                  25                  30

Arg Ala Ser Ser Phe Tyr Pro Arg Asn Ile Thr Leu Thr Trp Arg Gln
        35                  40                  45
```

```
Asp Gly Val Ser Leu Ser His Asn Thr Gln Gln Trp Gly Asp Val Leu
    50                  55                  60

Pro Asp Gly Asn Gly Thr Tyr Gln Thr Trp Val Ala Thr Arg Ile Arg
65                  70                  75                  80

Gln Gly Glu Glu Gln Lys Phe Thr Cys Tyr Met Glu His Ser Gly Asn
                85                  90                  95

His Gly Thr His
            100


<210> SEQ ID NO 39
<211> LENGTH: 100
<212> TYPE: PRT
<213> ORGANISM: Homo sapiens

<400> SEQUENCE: 39

Tyr Leu Lys Ser Gly Val Ala Ile Arg Arg Thr Val Pro Pro Met Val
1               5                   10                  15

Asn Val Thr Cys Ser Glu Val Ser Glu Gly Asn Ile Thr Val Thr Cys
            20                  25                  30

Arg Ala Ser Ser Phe Tyr Pro Arg Asn Ile Thr Leu Thr Trp Arg Gln
        35                  40                  45

Asp Gly Val Ser Leu Ser His Asn Thr Gln Gln Trp Gly Asp Val Leu
    50                  55                  60

Pro Asp Gly Asn Gly Thr Tyr Gln Thr Trp Val Ala Thr Arg Ile Arg
65                  70                  75                  80

Gln Gly Glu Glu Gln Arg Phe Thr Cys Tyr Met Glu His Ser Gly Asn
                85                  90                  95

His Ser Thr His
            100


<210> SEQ ID NO 40
<211> LENGTH: 100
<212> TYPE: PRT
<213> ORGANISM: Homo sapiens

<400> SEQUENCE: 40

Tyr Leu Lys Ser Gly Val Ala Ile Arg Arg Thr Val Pro Pro Met Val
1               5                   10                  15

Asn Val Thr Cys Ser Lys Val Ser Glu Gly Asn Ile Thr Val Thr Cys
            20                  25                  30

Arg Ala Ser Ser Phe Tyr Pro Arg Asn Ile Thr Leu Thr Trp Arg Gln
        35                  40                  45

Asp Gly Val Ser Leu Ser His Asn Thr Gln Gln Trp Gly Asp Val Leu
    50                  55                  60

Pro Asp Gly Asn Gly Thr Tyr Gln Thr Trp Val Ala Thr Arg Ile Arg
65                  70                  75                  80

Gln Gly Glu Glu Gln Arg Phe Thr Cys Tyr Met Glu His Ser Gly Asn
                85                  90                  95

His Ser Thr His
            100


<210> SEQ ID NO 41
<211> LENGTH: 114
<212> TYPE: PRT
<213> ORGANISM: Homo sapiens

<400> SEQUENCE: 41
```

```
His Ala Asp Cys Leu Gln Glu Leu Arg Arg Tyr Leu Lys Ser Gly Val
1               5                   10                  15

Val Leu Arg Arg Thr Val Pro Pro Met Val Asn Val Thr Arg Ser Glu
            20                  25                  30

Ala Ser Glu Gly Asn Ile Thr Val Thr Cys Arg Ala Ser Gly Phe Tyr
        35                  40                  45

Pro Trp Asn Ile Thr Leu Ser Trp Arg Gln Asp Gly Val Ser Leu Ser
    50                  55                  60

His Asp Thr Gln Gln Trp Gly Asp Val Leu Pro Asp Gly Asn Gly Thr
65                  70                  75                  80

Tyr Gln Thr Trp Val Ala Thr Arg Ile Cys Gln Gly Glu Glu Gln Arg
                85                  90                  95

Phe Thr Cys Tyr Met Glu His Ser Gly Asn His Ser Thr His Pro Val
            100                 105                 110

Pro Ser


<210> SEQ ID NO 42
<211> LENGTH: 90
<212> TYPE: PRT
<213> ORGANISM: Artificial Sequence
<220> FEATURE:
<223> OTHER INFORMATION: Synthetic Polypeptide

<400> SEQUENCE: 42

His Pro Val Val Lys Gly Gly Val Arg Ser Gln Ala Ala Asn Arg Ala
1               5                   10                  15

Glu Ala Thr Cys Arg Ala Ser Gly Phe Tyr Pro Trp Asn Ile Thr Leu
            20                  25                  30

Ser Trp Arg Gln Asp Gly Val Ser Leu Ser His Asp Thr Gln Gln Trp
        35                  40                  45

Gly Asp Val Leu Pro Asp Gly Asn Gly Thr Tyr Gln Thr Trp Val Ala
    50                  55                  60

Thr Arg Ile Cys Ser Asn Gln Asn Tyr Thr Cys Tyr Val Thr His Gly
65                  70                  75                  80

Asn Trp Thr Val Glu Ile Pro Ile Ser Val
                85                  90


<210> SEQ ID NO 43
<211> LENGTH: 92
<212> TYPE: PRT
<213> ORGANISM: Homo sapiens

<400> SEQUENCE: 43

Pro Pro Met Val Asn Val Thr Arg Ser Glu Ala Ser Glu Gly Asn Ile
1               5                   10                  15

Thr Val Thr Cys Arg Ala Ser Gly Phe Tyr Pro Trp Asn Ile Thr Leu
            20                  25                  30

Ser Trp Arg Gln Asp Gly Val Ser Leu Ser His Asp Thr Gln Gln Trp
        35                  40                  45

Gly Asp Val Leu Pro Asp Gly Asn Gly Thr Tyr Gln Thr Trp Val Ala
    50                  55                  60

Thr Arg Ile Cys Gln Gly Glu Glu Gln Arg Phe Thr Cys Tyr Met Glu
65                  70                  75                  80

His Ser Gly Asn His Ser Thr His Pro Val Pro Ser
                85                  90


<210> SEQ ID NO 44
```

-continued

```
<211> LENGTH: 91
<212> TYPE: PRT
<213> ORGANISM: Homo sapiens

<400> SEQUENCE: 44

His Pro Val Val Lys Gly Gly Val Arg Asn Gln Asn Asp Asn Arg Ala
1               5                   10                  15

Glu Ala Phe Cys Thr Ser Tyr Gly Phe Phe Pro Gly Glu Ile Gln Ile
            20                  25                  30

Thr Phe Ile His Tyr Gly Asp Lys Val Pro Glu Asp Ser Glu Pro Gln
        35                  40                  45

Cys Asn Pro Leu Leu Pro Thr Leu Asp Gly Thr Phe His Gln Gly Cys
    50                  55                  60

Tyr Val Ala Ile Phe Ser Asn Gln Asn Tyr Thr Cys Arg Val Thr His
65                  70                  75                  80

Gly Asn Trp Thr Val Glu Ile Pro Ile Ser Val
                85                  90


<210> SEQ ID NO 45
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 45

Ile Thr Val Thr Ser Arg Ala Ser Gly Phe Tyr Pro Trp Asn Ile Thr
1               5                   10                  15

Leu Ser Trp Leu Ser His Asp Thr Gln Cys Trp Gly Asp Val Leu Pro
            20                  25                  30

Asp Gly Asn Gly Thr Tyr Gln Thr Trp Val Cys Thr Arg Ile
        35                  40                  45
```

What is claimed:

1. A vaccine composition for treating cancer, the composition comprising (i) as an immunogenic component, an effective amount of a peptide *selected from the group* consisting of:

(a) amino acids [181] *179* to 274 of SEQ ID NO: 1, *having up to five amino acid modifications*;

(b) SEQ ID NO: 2, 11, 12, 13, 21 or 23, *wherein SEQ ID NO: 2 has up to six amino acid modifications, SEQ NO ID: 11, 13 and 21 have up to one amino acid modification and SEQ ID NO: 12 and 23 have up to two amino acid modifications*;

(c) SEQ ID NO: 11, 12, 13, 21 or 23, [further comprising] *having* 2, 4, 5, 6, 8, or 10 flanking amino acids on [either] the N-terminal [end of the peptide], the C-terminal [end of the peptide], or [both] the N-terminal [end] and the C-terminal [end] *ends* of the peptide,

*wherein SEQ ID NO: 11, 13 and 21 have up to one amino acid modification and SEQ ID NO: 12 and 23 have up to two amino acid modifications, and*

*wherein the flanking amino acids are amino acids adjacent to SEQ ID NO: 11, 12, 13, 21 or 23 in SEQ ID NO: 1 or 14, having up to three amino acid modifications*; [or]

(d) SEQ ID NO: 11, 12, 13, 21 or 23, [further comprising] *having* one or more flanking amino acids such that the [entire] peptide [consists of] *is* about 25 to 30 amino acids,

*wherein SEQ ID NO: 11, 13, 21 have up to one amino acid modification and SEQ ID NO: 12 and 23 have up to two amino acid modifications*; *and*

*wherein the flanking amino acids are amino acids adjacent to SEQ ID NO: 11, 12, 13, 21 or 23 in SEQ ID NO: 1 or 14, having up to three amino acid modifications; and*

(*e*) *amino acids 170 to 268 of SEQ ID NO: 14, having up to nine amino acid modifications;* the effective amount being an amount [effective to elicit] *that elicits* an immune response against the cancer;

[wherein flanking amino acids are amino acids adjacent to SEQ ID NO:11, 12, 13, 21 or 23 in SEQ ID NO: 1 or in SEQ ID NO: 14;] and (ii) an adjuvant selected from *the group consisting of* an oil-based adjuvant, a CpG DNA adjuvant, a mineral salt adjuvant, a particulate adjuvant, a mucosal adjuvant, a cytokine, a microbial derivative, an emulsion and a Toll-Like Receptor agonist.

2. The vaccine composition of claim 1, wherein the composition is effective to elicit an in vitro immune response against a MIC polypeptide.

3. The vaccine composition of claim 1, wherein the composition is effective to elicit an in vivo immune response against a MIC polypeptide.

4. The vaccine composition of claim 2, wherein the MIC polypeptide is not attached to a cell.

5. The vaccine composition of claim 1, wherein the composition is effective to elicit an immune response against a cancer cell expressing a MIC polypeptide.

6. The vaccine composition of claim [1] *2*, wherein the MIC polypeptide is a MICA or MICB polypeptide.

7. The vaccine composition of claim 1, wherein the cancer expresses MICA and/or MICB proteins.

8. The vaccine composition of claim 1, wherein the cancer is melanoma.

9. The vaccine composition of claim 1, wherein the peptide [consists of SEQ ID NO: 2, 5-13, 15-21 or 23] *is selected from the group consisting of:*

*SEQ ID NO: 2 or amino acids 170 to 268 of SEQ ID NO: 14, having up to six amino acid modifications;*

*SEQ ID NO: 9 or 19, having up to four amino acid modifications;*

*SEQ ID NO: 5, 7, 10, 15 or 20, having up to three amino acid modifications;*

*SEQ ID NO: 6, 8, 12, 16, 18 or 23, having up to two amino acid modifications; and*

*SEQ ID NO: 11, 13, 17 or 21, having up to one amino acid modification.*

10. [The] *A* vaccine composition[ of claim 1], wherein [the vaccine composition] *an immunogenic component* comprises a plurality of peptides *of claim 1,* consisting of *one or more of*:

(a) amino acids [181] *179* to 274 of SEQ ID NO: 1, *having up to five amino acid modifications*;

(b) SEQ ID NO: 2, 11, 12, 13, 21 or 23, *wherein SEQ ID NO: 2 has up to six amino acid modifications, SEQ ID NO: 11, 13 and 21 have up to one amino acid modification, and SEQ ID NO: 12 and 23 have up to two amino acid modifications*;

(c) SEQ ID NO: 11, 12, 13, 21 or 23, [further comprising] *having* 2, 4, 5, 6, 8, or 10 flanking amino acids on [either] the N-terminal end[ of the peptide], the C-terminal end[ of the peptide], or [both] the N-terminal [end] and the C-terminal [end] *ends* of the peptide,

*wherein SEQ ID NO: 11, 13 and 21 have up to one amino acid modification and SEQ ID NO: 12 and 23 have up to two amino acid modifications, and*

*wherein the flanking amino acids are amino acids adjacent to SEQ NO ID: 11, 12, 13, 21 or 23 in SEQ ID NO: 1 or 14, having up to three amino acid modifications*; [or]

(d) SEQ ID NO: 11, 12, 13, 21 or 23, [further comprising] *having* one or more flanking amino acids such that the [entire] peptide [consists of] *is* about 25 to 30 amino acids,

*wherein SEQ ID NO: 11, 13 and 21 have up to one amino acid modification and SEQ ID NO: 12 and 23 have up to two amino acid modifications; and*

*wherein the flanking amino acids are amino acids adjacent to SEQ ID NO: 11, 12, 13, 21 or 23 in SEQ ID NO: 1 or 14, having up to three amino acid modifications; and*

*(e) amino acids 170 to 268 of SEQ ID NO: 14, having up to nine amino acid modifications.*

11. The vaccine composition of claim 1, wherein the peptide is conjugated to a carrier protein.

12. The vaccine composition of claim 11, wherein the carrier protein is selected from tetanus toxin and diphtheria toxin.

13. The vaccine composition of claim 1, wherein the composition comprises a viral capsid protein engineered to display the [at least one] peptide [or plurality of peptides] on its surface.

14. The vaccine composition of claim 13, wherein the viral capsid protein is a hepatitis B capsid protein.

15. The vaccine composition of claim 1, wherein the composition is in the form of a polymer scaffold comprising the peptide.

16. The vaccine composition of claim 15, wherein the polymer scaffold is a porous, poly-lactide-co-glycolide (PLG) polymer scaffold.

17. The vaccine composition of claim 16, wherein the polymer scaffold further comprises one or both of a cytokine and a Toll-like receptor agonist.

18. The vaccine composition of claim 17, wherein the polymer scaffold further comprises autologous tumor cell lysates of a subject to be treated for cancer with the composition.

19. A method of treating cancer in a subject, the method comprising administering to a subject a vaccine composition of claim 1.

20. The method of claim 19, wherein the vaccine composition is administered as part of a therapeutic regimen.

21. The method of claim 20, wherein the therapeutic regimen further comprises one or more of radiation therapy, targeted therapy, immunotherapy, or chemotherapy.

22. The method of claim 19, wherein the vaccine composition is administered as part of a prime-boost strategy[ and the prime-boost strategy further comprises], *comprising* administering at least one[, preferably two] additional vaccine [compositions of the invention, each vaccine composition] *composition* comprising a different peptide selected from *the group of* peptides consisting of:

(a) amino acids [181] *179* to 274 of SEQ ID NO: 1, *having up to five amino acid modifications*;

(b) SEQ ID NO: 2, 11, 12, 13, 21 or 23, *wherein SEQ ID NO: 2 has up to six amino acid modifications, SEQ ID NO: 11, 13 and 21 have up to one amino acid modification and SEQ ID NO: 12 and 23 have up to two amino acid modifications*;

(c) SEQ ID NO: 11, 12, 13, 21 or 23, [further comprising] *having* 2, 4, 5, 6, 8, or 10 flanking amino acids on [either] the N-terminal[ end of the peptide], the C-terminal end[ of the peptide], or [both] the N-terminal [end] and the C-terminal [end] *ends* of the peptide,

*wherein SEQ ID NO: 11, 13 and 21 have up to one amino acid modification and SEQ ID NO: 12 and 23 have up to two amino acid modifications, and*

*wherein the flanking amino acids are amino acids adjacent to SEQ ID NO: 11, 12, 13, 21 or 23 in SEQ ID NO: 1 or 14, having up to three amino acid modifications*; [or]

(d) SEQ ID NO: 11, 12, 13, 21 or 23, [further comprising] *having* one or more flanking amino acids such that the [entire] peptide [consists of] *is* about 25 to 30 amino acids,

*wherein SEQ ID NO: 11, 13 and 21 have up to one amino acid modification and SEQ ID NO: 12 and 23 have up to two amino acid modifications; and*

*wherein the flanking amino acids are amino acids adjacent to SEQ ID NO: 11, 12, 13, 21 or 23 in SEQ ID NO: 1 or 14, having up to three amino acid modifications; and*

*(e) amino acids 170 to 268 of SEQ ID NO: 14, having up to nine amino acid modifications.*

23. The vaccine composition of claim 3, wherein the MIC polypeptide is not attached to a cell.

24. The vaccine composition of claim 1, wherein the mineral salt adjuvant is a mineral salt gel adjuvant.

25. The vaccine composition of claim 1, wherein the particulate adjuvant is a micro particulate adjuvant.

*26. The vaccine composition of claim 1, wherein*

*if SEQ ID NO: 11 has the flanking amino acids of elements (c) or (d), then the flanking amino acids have up to two amino acid modifications;*

*if SEQ ID NO: 12 has the flanking amino acids of elements (c) or (d), then the flanking amino acids have up to one amino acid modification;*

*SEQ ID NO: 2 has up to five amino acid modifications;*

*amino acids 170 to 268 of SEQ ID NO: 14 has up to four amino acid modifications;*

*if SEQ ID NO: 21 has the flanking amino acids of elements (c) or (d), then the flanking amino acids have tup to one amino acid modification;*

*if SEQ ID NO: 13 has the flanking amino acids of elements (c) or (d), then the flanking amino acids have up to one amino acid modification; and,*

*if SEQ ID NO: 23 has the flanking amino acids of elements (c) or (d), then the flanking amino acids have up to one amino acid modification.*

*27. The vaccine composition of claim 1, wherein*

*amino acid 171 of SEQ ID NO: 1 is replaced with a lysine;*

*amino acid 173 of SEQ ID NO: 1 is replaced with a glycine;*

*amino acid 179 of SEQ ID NO: 1, amino acid 4 of SEQ ID NO: 2, or amino acid 1 of SEQ ID NO: 11 is replaced with an arginine;*

*amino acid 204 of SEQ ID NO: 1, amino acid 29 of SEQ ID NO: 2, or amino acid 6 of SEQ ID NO: 11 is replaced with a glycine;*

*amino acid 208 of SEQ ID NO: 1, amino acid 33 of SEQ ID NO: 2, or amino acid 10 of SEQ ID NO: 11 is replaced with a tryptophan;*

*amino acid 213 of SEQ ID NO: 1 or amino acid 38 of SEQ ID NO: 2 is replaced with a serine;*

*amino acid 249 of SEQ ID NO: 1 or amino acid 74 of SEQ ID NO: 2 is replaced with an arginine;*

*amino acid 188 of SEQ ID NO: 14 or amino acid 9 of SEQ ID NO: 21 is replaced with an isoleucine;*

*amino acid 191 of SEQ ID NO: 14 is replaced with a lysine;*

*amino acid 254 of SEQ ID NO: 14 is replaced with a lysine; or*

*amino acid 266 of SEQ ID NO: 14 is replaced with a serine.*

* * * * *